United States Patent [19]

Wallach et al.

[11] Patent Number: 5,496,550
[45] Date of Patent: Mar. 5, 1996

[54] METHOD OF REDUCING THE OUTPUT OF EIMERIA OOCYSTS FROM A NEWBORN CHICK

[75] Inventors: Michael Wallach, Jerusalem; Thea Pugatsch, Maaleh Adumin; David Mencher, Jerusalem, all of Israel

[73] Assignee: Chilwalner, Tel-Aviv, Israel

[21] Appl. No.: 108,763

[22] Filed: Aug. 17, 1993

Related U.S. Application Data

[63] Continuation of Ser. No. 642,219, Jan. 16, 1991, abandoned, which is a continuation-in-part of Ser. No. 310,603, Feb. 14, 1989, abandoned, which is a continuation-in-part of Ser. No. 155,245, Feb. 12, 1988, abandoned, which is a continuation-in-part of Ser. No. 896,611, Aug. 14, 1986, abandoned.

[30] Foreign Application Priority Data

Aug. 13, 1987 [CA] Canada ..................... 544427

[51] Int. Cl.$^6$ ............... A61K 39/00; A61K 39/012; A61K 39/002; A61K 39/35
[52] U.S. Cl. .................. 424/184.1; 424/267.1; 424/271.1; 424/276.1; 435/69.1; 435/69.3
[58] Field of Search ............... 424/88, 92, 267.1, 424/271.1, 265.1, 276.1; 435/69

[56] References Cited

FOREIGN PATENT DOCUMENTS 0256536  2/1988  European Pat. Off. ...... A61K 39/012

OTHER PUBLICATIONS

Gilbert et al Avian Disease 32: 688–694, 1988.
Losch et al J. Vet Med B. 33: 609–619, 1986, The Chicken Egg, an Antibody Source.
Kowalczyk et al, Immunology 54: 755–762, 1985, Quantitation of Maternal–Fetal Egg Transport in the Chicken.
Song et al, The J of Immunology 135: 3354–3359, 1986.
Rose et al Parasitology 63: 299–313, 1971.

*Primary Examiner*—Hazel F. Sidberry
*Attorney, Agent, or Firm*—John P. White

[57] ABSTRACT

This invention provides a method of reducing the output of *Eimeria oocysts* from a newborn chick which comprises administering to a laying hen at a suitable time prior to the hen laying a fertilized egg an amount of native or recombinant antigenic protein present in gametocytes of the Eimeria spp. effective to induce in the hen an immune response conferring protection via maternal immunity against infection or transmission by the Eimeria spp. in the offspring chick.

12 Claims, 19 Drawing Sheets

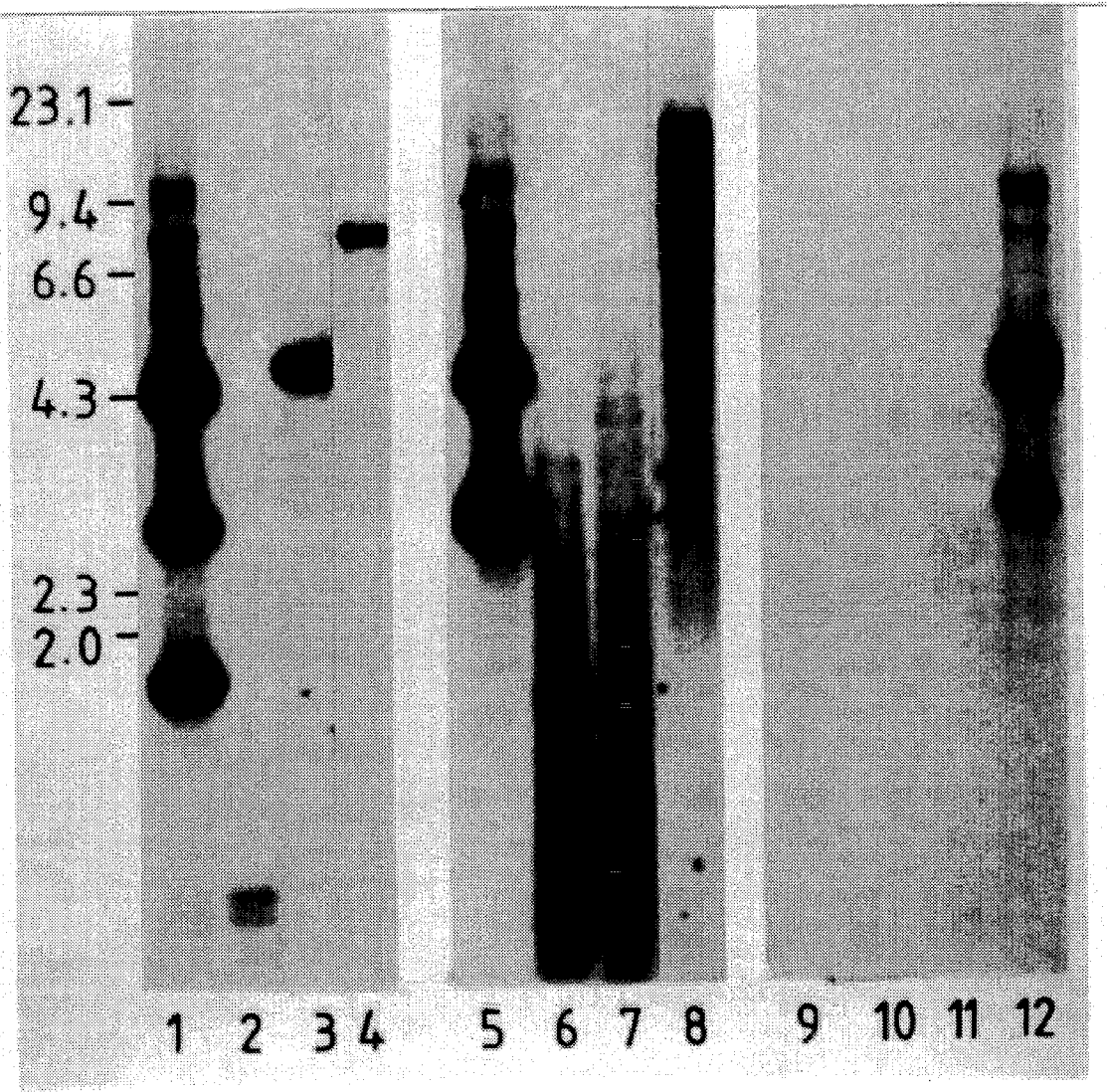

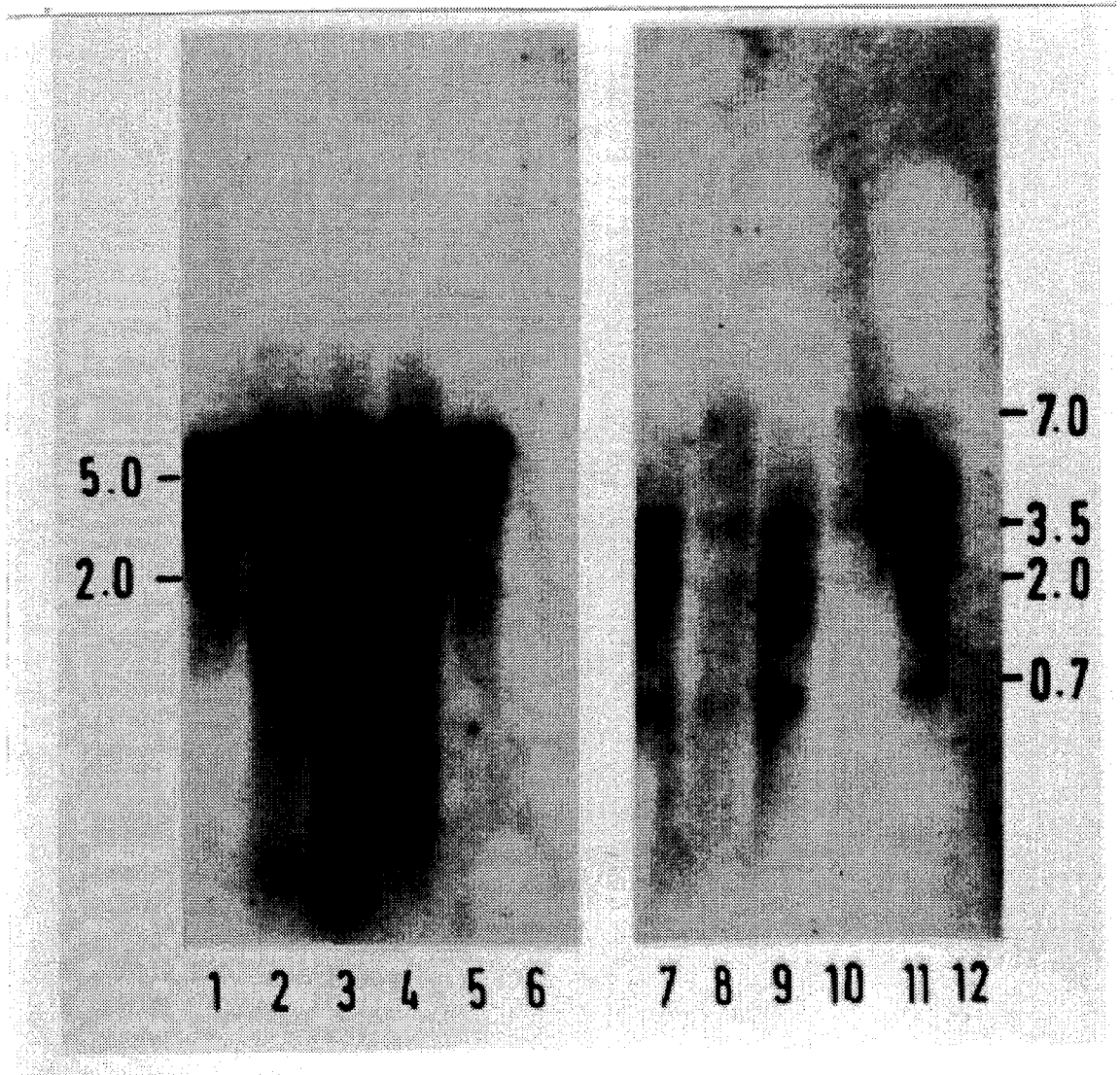

FIGURE 11

```
                    10                          30                         50
5' GTG GTG ATT GAA TCT GCT CCA GCC AAG ATG GCT CAC CCT CCT GTG GTG ATT GAG TCT GCT
   Val Val Ile Glu Ser Ala Pro Ala Lys Met Ala His Pro Pro Val Val Ile Glu Ser Ala 70                          90                        110
   CCG GTC GAG GTG GTC CAT CCT CCT ATG GTG ATT GAA TCT GCT CCA CCC AAG ATG GCT CAA
   Pro Val Glu Val Val His Pro Pro Met Val Ile Glu Ser Ala Pro Pro Lys Met Ala Gln 130                         150                        170
   CCT CCG ATG GTG ATT GAG TCT GCT CCA CCC AAG ATG GCT CAA CCA CCT ATG GTG ATT GAG
   Pro Pro Met Val Ile Glu Ser Ala Pro Pro Lys Met Ala Gln Pro Pro Met Val Ile Glu 190                         210                        230
   TCG GCT CCC GTC GAG GTG GTC CAT CCT CCT ATG GTG ATG GAA GCC GCT CCC ACC GTG AAG
   Ser Ala Pro Val Glu Val Val His Pro Pro Met Val Met Glu Ala Ala Pro Thr Val Lys

GGA AGA TAC CTC GCT GCT GAG GAT GAG GTG GAA GAG CAG TTT GAA TCG AAC AG 3'
   Gly Arg Tyr Leu Ala Ala Glu Asp Glu Val Glu Glu Gln Phe Glu Ser Asn
```

Nucleic acid sequence of the first 293 nucleotides of clone pEM 250/14. Note the presence of a 14 amino acid repetitive sequence in the single translated open reading frame.

FIGURE 12

```
5' C CTG CAG GTT GTA CTA AGA GCG CTT TAT GAC TAT CGG GAG CTC AAA TGC GGC TCA GCA TGC
    Leu Gln Val Val Leu Arg Ala Leu Tyr Asp Tyr Arg Glu Leu Lys Cys Gly Ser Ala Cys
             10                      30                          50

CGG AAC GTG GGC ATT TTG GTA CAC GGA GGT ATC ACC TCG AGC GAA TGG GCG GGG GTC TTT
  Arg Asn Val Gly Ile Leu Val His Gly Gly Ile Thr Ser Ser Glu Trp Ala Gly Val Phe
           70                      90                         110

CCG CAA ACA AGC GTT CCA AAA CCT AAG GTG GAA AAC TGT TCA GTT GCA TTT AAT TAC
  Pro Gln Thr Ser Val Pro Lys Pro Lys Val Glu Asn Cys Ser Val Ala Phe Asn Tyr
          130                     150                         170

GCT TTT GTA AAT ACC 3'
  Ala Phe Val Asn Thr
        190
```

Nucleic Acid sequence of the last 196 nucleotides of clone pEM 250/14. The single open reading frame is translated into the amino acid sequence shown below the nucleotide sequence. A potential N-linked glycosylation site (Asn-Cys-Ser) is underlined.

FIGURE 13

```
5' CC TCT CAT ACG ACC TAA TAC GTA AAA GAG AAA ATG TTG TTG CTG CCT TTG CTG CAG TCA
              10              30              50              70              90              110
AGA     TAA GAG CAG CAA TTG AGG CAG ATG GGC CGC ATT ATA CTG CTG CAG CAG CTA CCA GCT
                                        Met Gly Arg Ile Ile Leu Leu Gln Gln Leu Pro Ala
                130                150                170

GCA GCT GCT GCA ACT GCT GAT GCA ACT GCT GCT GCA CCT GCT GCT GCT GGT GCT
Ala Ala Ala Ala Thr Ala Asp Ala Thr Ala Ala Ala Pro Ala Ala Ala Gly Ala
    190                210                230

GCT GCT GCA GCA GAA CAG CAA TTG AGG AAA AGA GCA GCA GTA CCT TAC ATG CCC AAC
Ala Ala Ala Ala Glu Gln Gln Leu Arg Lys Arg Ala Ala Val Pro Tyr Met Pro Asn
    250                270                290

TTG GTG CGT CTC CAG TGT CTC CTG TTG TTA TAC TTG ATC TTG CAG TCA GTC TTC ATC
Leu Val Arg Leu Gln Cys Leu Leu Leu Leu Tyr Leu Ile Leu Gln Ser Val Phe Ile
    310                330                350

CGT ACC CAA TGA GGA TCG ACG ATT TTG TTT TTG CTT CTT GCC GAG CCT CTT CTT GAG GTT
Arg Thr Gln End
    370                390                410

TAA ACC CTT AAT GGA ACC CAT CTT CAC CAA CAG CTG CGC AGC AGC AAA CCC TCT ATT TAA TAA AAT CTA ACC TCT ATT AAT TGC CTT AAA CCC TCT ATT TAA TAA AAT CTA ACC
                                                                            AAA ATA ATT GGG GTG
    430                450                470

TAT AGG CAG TTC TTG TTT ATT ATT AAT TGC CTT AAA CCC TCT ATT TAA TAA AAT CTA ACC TG 3'
```

Nucleic acid sequence of the entire 484 base pairs of clone pEM 56/2. The initiation and termination codons are boxed and the potential polyadenylation signal is overlined. The open reading frame is translated into the 76 amino acid polypeptide. This small polypeptide is very rich in alanine (30%) and leucine (18%).

FIGURE 14A

```
        10                  30                                  50
CTG CAG CAC CAC CAA CAT ATC ATA CTA CAG CAG CAA CAA CAT CAT CCT CCT
Leu Gln His His Gln His Ile Ile Leu Gln Gln Gln Gln His His Pro Pro
                    70                  90                         110
CCT GCT GCT GTA CTT GTT GCT GCT GCT CCT CCA GAT AAA GAA CAA TTT GCT GCT GCT
Pro Ala Ala Val Leu Val Ala Ala Ala Pro Pro Ala Asp Lys Glu Gln Phe Ala Ala Ala
                        130                                 150                    170
GCT GCT GCA CCT ATC CCT ATT GCT GCA GCA AGC AAA GAA ACA CCT ATA GAC ATG ATG
Ala Ala Ala Pro Ile Pro Ile Ala Ala Ala Ser Lys Glu Thr Pro Leu Ile Asp Met Met
                        190                                 210                    230
AGT AAA TAA ACA CAT AAA TAA ATT AAT AAA TAA ATA AAT AAA TAA ATA TAA TTT ATT TAT
Ser Lys END
                250                                 270                 290
TTA TAT TTA TTT ATT TAT TTA TTT ATT TGG TGT CTT TGT CGA TTC ATG TGC ATG CAT ATT
                        310                                 330                        350
CAC TTC AAA AAA GCC CGC AAA AAA TAA TGC AAG CAG TGC ATG CAA ATA AGC ATG CAT GCA
                        370                                 390                        410
AGC ATT TCT TTC TTC TTT TTT CTT CTT CTT TCT TCT CTT TTA TTA AGA GAG
                        430                                 450
AAA TAA ATA ACT CTA TTT ACT CAT GCA TAT TTA AAG TGT ATG AAAA...3'
```

Nucleic acid sequence of the entire 498 base pairs of clone pEM 56/3. As can be seen this cDNA clone comes from the 3' part of the mRNA and contains only a small portion of the coding region, and the entire 3' untranslated region to the poly A tail. There are two possible open reading frames of 186 nucleotides (14A) and 169 nucleotides (14B) which have been translated into the corresponding polypeptides. In Figure 14B there is one potential N-linked glycosylation site (Asn-Ile-Ser) which is underlined.

FIGURE 14B

```
                                                    50
TGC AGC ACC ACC AAC ATA TCA TAC AGC AGC AAC ATC ATC CTC CTC
Cys Ser Thr Thr Asn Ile Ser Tyr Ser Ser Asn Ile Ile Leu Leu
         70                      90                     110

CTG CTG TAC TTG CTC CTG TTG CTG CAG ATA AAG AAC AAT TTG CTG CTG CTG
Leu Leu Tyr Leu Leu Leu Leu Leu Gln Ile Lys Asn Asn Leu Leu Leu Leu
        130                     150                     170

CTG CTG CAC CTA TCC CTA TTG CTG CAA GCA AAG AAA CAC CTC TTA TAG ACA TGA TGA
Leu Leu His Leu Ser Leu Leu Leu Gln Gln Ala Lys Lys His Leu Leu Leu End
        190                     210                     230

GTA AAT AAA CAC ATA AAT AAA TTA ATA AAT AAA TAT AAT TTA TTT ATT
                    250                     270                     290

TAT ATT TAT TTA TTT ATT TAT TTA TTT GGT GTC TTT GTC GAT TCA TGT GCA TGC ATA TTC
                    310                     330                     350

ACT TCA AAA AAG CCC GCA AAA AAT AAT GCA AGC AGT GCA AAA TAA GCA TGC ATG CAA
                    370                     390                     410

GCA TTT CTT TCT TCT TTT TTC TTC TTT CTT CTC TTT TAT TAA GAG AGA
                    430                     450

AAT AAA CTC TAT TTA CTC ATG CAT ATT TAA AGT GTA TG AAAA...3'
```

METHOD OF REDUCING THE OUTPUT OF EIMERIA OOCYSTS FROM A NEWBORN CHICK

This application is a continuation of U.S. Ser. No. 07/642,219, filed Jan. 16, 1991, now abandoned, which is a continuation-in-part of U.S. Ser. No. 07/310,603, filed Feb. 14, 1989, now abandoned, which is a continuation-in-part of U.S. Ser. No. 07/155,245, filed Feb. 12, 1988, now abandoned, which is a continuation-in-part of U.S. Ser. No. 06/896,611, filed Aug. 14, 1986, now abandoned, the contents of which are hereby incorporated by reference into the present application.

BACKGROUND OF THE INVENTION

Throughout this application, various publications are referenced by Arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

The organisms which cause the disease known as "coccidiosis" in chickens belong to the phylum Apicomplexa, class Sporozoa, subclass Coccidia, order Eucoccidia, suborder Eimeriorina, family Eimeriidae, genus Eimeria. Within the Eimerian genus there are many species, several of which are pathogenic in chickens. The species of major concern to the chicken industry are *Eimeria tenella, Eimeria maxima, Eimeria acervulina, Eimeria necatrix* and *Eimeria brunetti.*

Coccidiosis has become a major economic problem in the chicken industry over the past few decades, mainly due to the overcrowding of chicken houses and drug resistance. The rearing of chickens under crowded conditions on a litter floor provides optimal conditions for the growth and spread of coccidia. Under such circumstances, sanitary control becomes nearly impossible and the farmer must rely on the effectiveness of coccidiostat drugs. However, drugs must be kept in the feed at all times and therefore are very expensive, certain drugs have costly side effects, and drug resistance has become a major problem under field conditions. Several large suppliers of these agents have come to realize that perhaps the only viable approach to the control of coccidiosis is by vaccine development.

The Eimerian parasites undergo a complex life cycle in the mucosa of the intestinal tract. They show a great deal of specificity both in terms of the species they infect and in their location within the intestine. In fact, site specificity of infection is used as the major criterion for diagnosis. Other parameters for diagnosis include size and shape of oocysts, characteristics of the infected intestine, weight loss, and skin pigmentation changes.

The life cycle of Eimeria is very similar to that of the hemosporidian parasites (i.e. plasmodium) except for the lack of an arthropod vector. Oocysts sporulate on the litter floor producing four sporocysts, each containing two sporozoites. These are ingested by the chicken and the sporozoites are released by the mechanical grinding of the oocysts in the gizzard and the subsequent digestion of the sporocyst wall by proteolytic enzymes. Sporozoites then invade lymphocytes and go on to invade epithelial cells where the asexual cycle begins. The parasite goes through 2–4 cycles of replication and division (each species having a defined number of divisions) leading to a production of large numbers of merozoites. After the final cycle of merozoite production the sexual cycle begins with the production of macrogametocytes (female) and microgametocytes. The macrogametocyte is characterized by the production of wall forming bodies which are involved in the production of the oocyst wall. Microgametocytes contain the components involved in the formation of microgametes which bud off from the surface of the intracellular parasite. Microgametes are flagellated and are responsible for the fertilization of the macrogamete. A zygote is formed which matures into the oocyst by fusion of the wall forming bodies and condensation of the nucleus. Oocysts are secreted in the feces, thus completing the cycle.

A single infection with Eimeria can lead to protection against subsequent reinfection with the same strain of that species. This finding was used as the basis for producing a live vaccine against coccidiosis. Small numbers of oocysts from all the major pathogenic species are provided either in water (COCCIVAC™) or are encapsulated in a water soluble polysaccharide (British patent GB 2,008,404A) giving rise to subclinical infections. However, even with small numbers of oocysts severe outbreaks of coccidiosis have occurred and farmers are reluctant to introduce live, pathogenic parasites into their chicken houses.

In order to solve the problem of introducing pathogenic coccidia into a live vaccine, several laboratories have been working towards the production of live attenuated vaccines. By repeated passages in egg embryos or isolation of precocious lines (i.e. parasites that go through the life cycle in five days rather than six or seven), much less virulent and nonpathogenic strains of most of the major species have been isolated. Good protection has been observed using this approach, however there are still problems which include: shelf life of live parasites; back mutations of attenuated lines to pathogenic strains; strain variation especially in the case of *Eimeria maxima;* inability to protect for long periods of time; and introduction of any live coccidia into a chicken house would be resisted by farmers. With all these problems, the attenuated live vaccine may be used in the field until a more defined, noninfective, subunit vaccine can be developed.

In the area of subunit vaccines the extracellular stages of the life cycle (the sporozoite, the merozoite and the gametes—micro and macro) are the most vulnerable to immune attack. The sporozoite is the first stage of development after the parasite is released from the oocyst and after a short time in the lumen invades a lymphocyte. In natural infections, high titers of antibody to sporozoites have been found and this stage is considered to be most promising for vaccine development. As a result, several laboratories have been working towards a sporozoite vaccine.

*E. tenella* sporozoite extracts as well as supernatants of ground, sporulated oocysts were shown to protect broilers up to 7 weeks of age from challenge infections (1). In work using monoclonal antibodies, results have indicated that preincubation of sporozoites with monoclonal antibodies directed against surface antigens and injection into the cloaca of chickens, can give partial protection against the infection. Antigens recognized by these monoclonal antibodies have been identified by Western blotting and one of them, a protein of 25,000 molecular weight, has been cloned and sequenced (European patent publication No. 0 164 176, published Dec. 11, 1985). This antigen was tested as an immunogen for protection against challenge infections where partial immunity was observed. American Cyanamid has also made several monoclonal antibodies to sporozoite surface antigens, some of which exhibited partial protection against *Eimeria tenella* infections (European patent publication No. 0 135 712, published Apr. 3, 1985, and European patent publication No. 0 135 073, published Mar. 27, 1985). The reason that purified antigens gave only partial protection in those studies may be due to the finding, that *Eimeria tenella* sporozoites can cap and shed their surface antigens, which is an important mechanism of host immune invasion (2). Thus, it appears that the sporozoite stage may contain some antigens which can give partial protection, however, it seems unlikely that full protection will be achieved using only a sporozoite vaccine.

The role of antibody in the protective immune response against Eimeria in chickens has received a great deal of attention. In several studies carried out by Rose & Long (3–8), it was found that serum taken from birds which had recovered from infections with *E. tenella* or *E. maxima* can give passive protection against challenge infections with these species. Based on these results and similar to the studies described above, Rose & Long immunized chickens with extracts of sporozoites and merozoites and the sera were tested for their effect on invasion by sporozoites in vitro and protection in vivo. In contrast to the active immunization results described above and in spite of the fact that these sera were capable of neutralizing sporozoites and merozoites in vitro, birds which were immunized with extracts of sporozoites or merozoites showed no resistance to oral infections with *E. tenella* oocysts. Furthermore, sera from the same immunized birds could not be used to protect naive chickens. Thus, those authors concluded that antibody may play only a minor role in protection against Eimeria in spite of their passive immunization results (3–8).

In previous reports maternal antibody was shown to play an important role in resistance to coccidial infection (4). In one experiment laying hens were given multiple infections with *E. tenella* and the offspring were challenged with oocysts from the same strain and compared with chicks from uninfected layers used as a control. It was found that the chicks hatched from immune layers had a 75% lower oocyst output as compared to the control. These results corroborate the passive immunization studies described by Rose and her coworkers (3–8), and based on the parameter of oocyst output show that maternal antibody plays an important role in protective immunity.

A vaccine using antigens from the merozoite stage is also being tested (European patent publication No. 0 135 073). Several laboratories are making monoclonal antibodies to merozoite surface antigens in order to test their ability to inhibit invasion in vitro and in vivo. Most of these antigens were also found to be present in sporozoites as well as in different Eimerian species (9,10). In vivo protection results using these monoclonal antibodies again only showed partial inhibition and only with very low numbers of parasites (challenge dosage of 200 sporozoites) (European patent publication No. 0,135,172). Similar studies have been carried out for malarial merozoite surface antigens where excellent results using monoclonal antibodies to inhibit invasion in vitro have been obtained (11,12), however poor results were found in vivo. Problems of antigenic variation and diversity at this developmental stage of malaria is probably the major reason. Currently, attempts are being made to identify constant epitopes within these antigens and produce small peptedes which contain the important antigenic determinants.

The gametocyte stages of Eimerian development are the most difficult to analyze and very little has appeared in the literature regarding gamete subunit vaccines due to the following reasons: despite much effort Eimerian gametes have never been isolated before and, therefore, new methods need to be developed in order to study this developmental stage at the molecular level; no efficient in vitro system has been described for working with the sexual stages of Eimerian development; and most previous reports by leading authors in the field have led to the conclusion that gametes play little or no role in protective immunity (13,14,30).

In work carried out by Rose on immunity to *E. maxima* (5–8), it was found that sera taken from recovered birds 14 days post infection can give passive protection of up to 93% (based on oocyst output) against challenge with *E. maxima*, and these sera by Ouchterlony were found to precipitate an antigen prepared from mucosa containing gametocyte stages and not with sporozoite proteins (8). However, in these studies no direct proof of gametes playing a role in protective immunity was reported, nor were experiments done using the recovered antisera to identify the antigens seen by Ouchterlony. In fact, gametocytes were not purified and tested; only a mucosal extract was tested. In subsequent work Rose and others did not conclude that sexual stages, i.e., gametes play any role in induction of protective immunity to *E. maxima* (14) or to any other Eimeria species in spite of the results they obtained. In order to assess the role of the recovered sera in protective immunity, studies at the molecular level are required to characterize the proteins being recognized and the particular stage(s) at which they are being synthesized.

In studies carried out on malarial gametocytes and gametes, it was found that antigens from these stages can be used to protect birds against transmission of the disease (15). Furthermore, monoclonal antibodies to these antigens can be used to block the further development of the malaria parasite (16).

One of the prerequisites for studying the role of gametocytes in protective immunity, is their isolation. No prior report has been made on isolating gametocytes of Eimeria. Most of the published work done on gametocytes prior to the subject invention involved using electron microscopy to observe the growth and development of gametocytes in vivo. No studies have been published on the identification of stage specific gametocyte antigens. In early attempts to analyze gametocyte antigens in either whole infected intestine or partially purified preparations, little or no difference was seen by SDS polyacrylamide gel electrophoresis between infected intestine and normal intestine. It was therefore necessary for us to develop a method for isolation of gametocytes to a very high degree of purity in order to carry out molecular studies.

Once gametocytes are isolated they can be used to identify and isolate the protective transmission blocking antigens of *Eimeria maxima*. Monoclonal and polyclonal antibodies can be raised against these antigens and used to passively protect chicks as well as to identify cDNA clones in a gametocyte cDNA expression library. Once the antigens are isolated (either native or cloned) they can be tested for their ability to elicit protective immunity in young chicks.

One of the difficulties in vaccinating young chicks however, is the lack of a mature immune system capable of responding to the administered antigens in a subunit vaccine. Another approach whereby large amounts of specific antibody can be provided to newborn chicks is through maternal immunization of laying hens. Gametocyte antigens can be used to immunize laying hens who thereby provide large amounts of specific protective anti-gametocyte antibody to their offspring chicks via yolk antibodies. Furthermore, by providing such antibody against gametocyte antigens, newborn chicks are susceptible to infection by the asexual stages of development. These asexual stage antigens act to induce protective immunity against invasion by sporozoites and merozoites in subsequent reinfection, while the anti-gametocyte antibodies act to reduce oocyst output by blocking either the growth, development and/or fertilization of gametocytes.

The concept of using defined coccidial antigens to immunize chicks against infection via maternal immunity is a novel one. The work described above by Rose & Long on maternal immunity (4), only relates to the effect of live infections on laying hens and transfer of resistance via maternal immunity to the chicks. In those studies no mention was made of the use of native or cloned stage specific antigens to induce protective immunity, nor was the mechanism by which the live infection induced protection in offspring chicks analyzed.

The present invention involves a method for the isolation of $E.$ $maxima$ macrogametocytes and microgametocytes. The isolation procedure of the present invention allows for the purification, to a very high degree (over 90%) of $E.$ $maxima$ gametocytes, with little or no host contamination (based on SDS-polyacrylamide gel electrophoresis analysis).

The present invention also concerns the identification of protective gametocyte antigens and the RNA which encodes them. These antigens were found to give partial protection against challenge infections with $E.$ $maxima$ in vivo. Antisera from immunized and recovered chickens as well as immunized mice, guinea pigs, and rabbits, have been used to identify the antigens involved by Western blotting and immune precipitation techniques. These antisera as well as monoclonal antibodies and soybean lectin were used to isolate the antigens from protein extracts of gametocytes, as well as to screen a cDNA expression library prepared from gametocyte mRNA. In addition, these antibodies were used to passively immunize chickens against challenge infections, while the antigens were used to actively immunize chicks.

The present invention provides a method of conferring upon a newborn chick maternal immunity (antibodies) against infection and/or transmission of an Eimeria spp. which comprises administering to a laying hen at a suitable time prior to the hen laying a fertilized egg an amount of a native or recombinant antigenic protein present in gametocytes of the Eimeria spp. effective to induce in the hen an immune response conferring protection via maternal immunity against infection and/or transmission of an Eimeria spp. in the offspring chick.

SUMMARY OF THE INVENTION

The present invention provides a method of conferring upon a newborn chick maternal immunity (antibodies) against infection or transmission of an Eimeria spp. which comprises administering to a laying hen at a suitable time prior to the hen laying a fertilized egg an amount of a native or recombinant antigenic protein present in gametocytes of the Eimeria spp. effective to induce in the hen an immune response conferring protection via maternal immunity against infection or transmission of an Eimeria spp. in the offspring chick.

BRIEF DESCRIPTION OF THE FIGURES

FIG. 3A presents a preparative Western Blot containing gametocyte proteins where individual strips were reacted with a variety of recovered chicken sera (Lanes 1 to 20) and as a control chicken anti-cytochrome serum (Lane 21).

FIG. 3B presents a preparative Western Blot containing gametocyte proteins which were reacted with a variety of normal chicken sera (Lanes 1 to 8) and compared to antigens detected by recovered chicken serum (Lane 9).

FIG. 3C presents a preparative Western Blot containing gametocyte proteins which were reacted with chicken serum taken at various times post-infection. Birds were infected with $1\times10^4$ $E.$ $maxima$ oocysts and blood was taken on day 0 (Lane 1), day 6 (Lane 2), day 11 (Lane 3) and day 14 (Lane 4) post-infection.

FIG. 3D presents a preparative Western Blot containing gametocyte proteins which were reacted with newborn chicken sera (Lane 2) and recovered chicken serum (Lane 1). Numbers at the right indicate the major immune detectable bands.

FIG. 8 shows the results from a hybrid select translation experiment. DNA was prepared from the plasmid clones AL-4 (a control p bluescript plasmid containing no insert) and pEM 82/4 (prepared from the phage lambda EM 82/4) and were bound to nitrocellulose filters. Total gametocyte RNA was allowed to hybridize to the filters and after several hours of hybridization the filters were washed. The bound RNA was eluted from the filters by boiling in $H_2O$, it was ethanol precipitated and the hybrid selected RNA was then translated in a rabbit reticulocyte cell-free system. The translation products directed by total gametocyte RNA (Lane 1), RNA eluted from AL-4 containing filters (Lanes 2–4), and RNA eluted from pEM 82/4 containing filters (Lanes 5–7) were analyzed by polyacrylamide gel electrophoresis and autoradiography. Numbers at the left indicated molecular weight marker proteins (x $10^{-3}$) and the arrow points to the 250 Kd hybrid selected translation product.

FIG. 9 presents the results of a Southern blot of *E. maxima* DNA hybridized with either clone pEM 250/14 (panel A), pEM 56/2 (panel B), or p Bluescript DNA (panel C). Lanes 4, 8 and 9 are *E. maxima* DNA cut with the restriction enzyme EcoRI, lanes 3, 7 and 10 are *E. maxima* DNA cut with the enzyme Pst I, lanes 2, 6 and 11 are *E. maxima* DNA cut with Alu I. Lanes 1, 5 and 12 contain 1 nanogram of clone pEM 250/14 cut with EcoRI. Numbers at left indicate the sizes in kilobases of the lambda marker fragments.

FIG. 10A presents the results of a Northern blot using clone pEM 250/14 as a probe. Lanes 1 and 3–5 contain total RNA extracted from whole gametocyte infected intestines taken 134 hours post infection with 10,000 *E. maxima* sporulated oocysts. Lane 2 contains RNA extracted from purified gametocytes and lane 6 contains total RNA from uninfected chicken intestine. Numbers at left indicate the ribosomal RNA markers in kilobases, and the numbers at right indicate the sizes of the major mRNA bands.

FIG. 10B presents the results of a Northern blot using clone pEM 56/2 as a probe. Lanes 7 and 9–11 contain total RNA extracted from whole gametocyte infected intestines taken 134 hours post infection with 10,000 *E. maxima* sporulated oocysts. Lane 8 contains RNA extracted from purified gametocytes and lane 12 contains total RNA from uninfected chicken intestine. Numbers at left indicate ribosomal RNA markers in kilobases, and the numbers at right indicate the sites of the major mRNA bands.

FIGS. 11, 12, 13, 14 show the DNA sequences (some complete and others partial) of clones lambda EM 82/4, p EM 250/14, p EM 56/2 and p EM 56/3 respectively. Open reading frames and restriction enzyme sites are indicated, and the predicted amino acid sequences are shown.

DETAILED DESCRIPTION OF THE INVENTION

Figure 1:
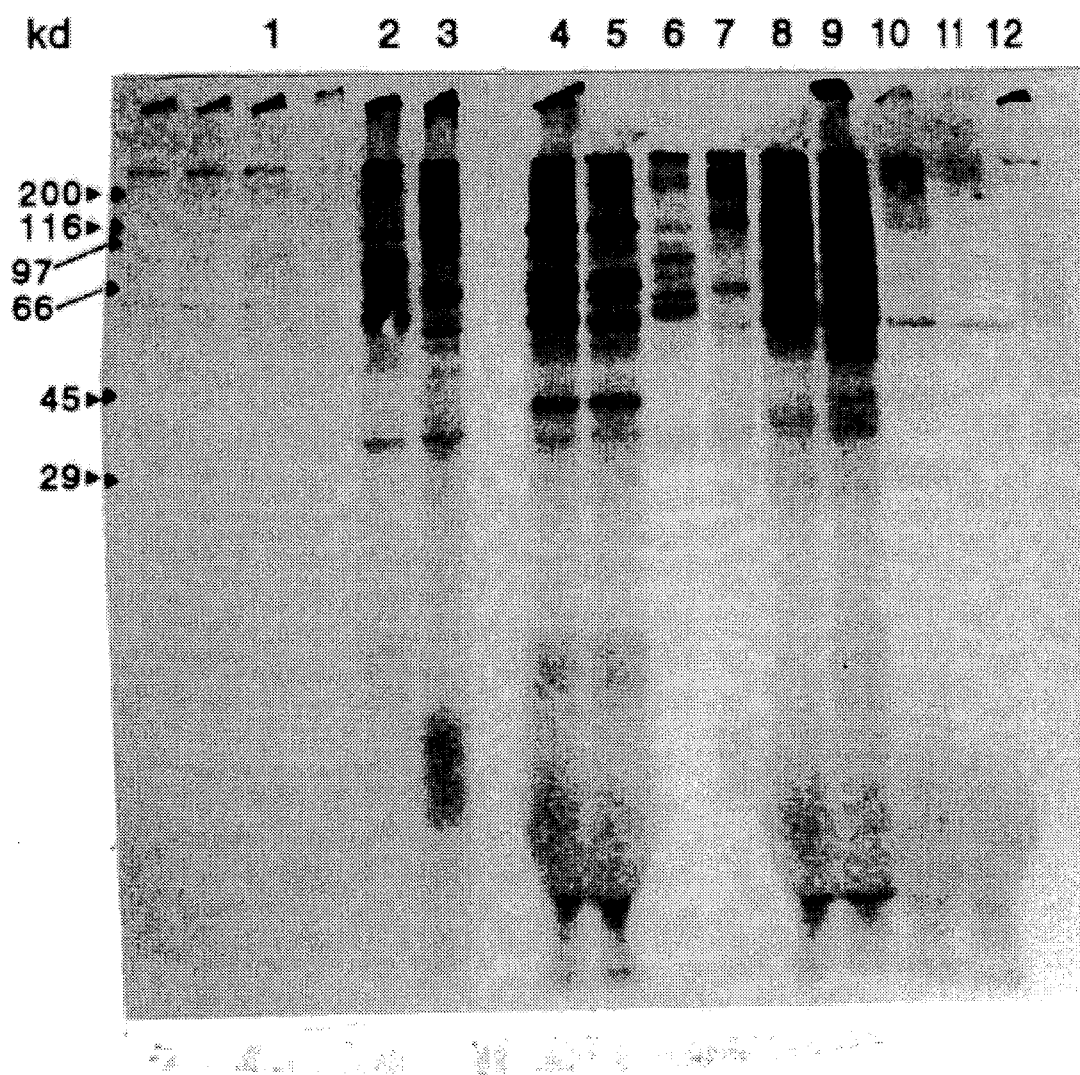
FIG. 1 depicts the SDS-PAGE of metabolically labeled and cell-free translated gametocyte and host proteins. Metabolically labelled ($^{35}$S-methionine incorporation) protein extracts of purified $E.$ $maxima$ gametocytes (Lanes 2,6) and chick uninfected intestinal tissue (Lanes 3,7) were compared with the pattern of labeled proteins from cell-free translation of mRNA from purified gametocytes (Lanes 4,5,10), whole infected (Lane 9) or uninfected chick intestine (Lane 8). Protein size markers (205 Kd, 116 Kd, 97.5 Kd, 66 Kd, 45 Kd and 30 Kd) are indicated with black marker.

The present invention provides a method of conferring upon a newborn chick maternal immunity (antibodies) against infection and/or transmission of an Eimeria spp. which comprises administering to a laying hen at a suitable time prior to the hen laying a fertilized egg an amount of a native or recombinant antigenic protein present in gametocytes of the Eimeria spp. effective to induce in the hen an immune response conferring protection against infection and/or transmission of an Eimeria spp. in the offspring chick.

In one embodiment of the invention, Eimeria spp. is *Eimeria maxima*.

The antigenic protein present in gametocytes from the Eimeria spp. may be any surface protein capable of eliciting an immune response. In general, the protein will be selected from the group consisting of proteins having molecular weight of 250±20 Kd, 116±10 Kd, 82±10 Kd, 78±5 Kd, 56±5 Kd, 54±5 Kd, 52±5 Kd, 43±5 Kd, and 36±5 Kd. In presently preferred embodiments of the invention, the antigenic protein comprises a protein having a molecular weight of about 56 Kd, a protein having a molecular weight of about 82 Kd, or a protein having a molecular weight of about 250 Kd.

The antigenic proteins used in the method of this invention maybe derived or recovered from gametocytes of the Eimeria spp. against which protection is being sought. Alternatively, the antigenic proteins may correspond to such proteins but be produced by conventional genetic engineering methods well known in the art. In the latter case such proteins may vary by the presence, absence or substitution of one or more amino acids as compared with the naturally occurring proteins, provided only that such recombinant proteins have substantially the same amino acid sequence as the immunological properties of the naturally occurring proteins.

In one embodiment of the invention, the effective immunizing amount of antigenic protein is between about 5 ng and about 5000 ng. In a presently preferred embodiment of the invention, the effective amount of antigenic protein is between about 50 ng and about 100 ng.

Hens which have been immunized according to the method of the subject invention provide protection to their offspring chicks from the day of the chicks hatching against challenge with sporulated Eimeria spp. oocysts.

A booster may be administered to either the hens or young chicks and may comprise live Eimeria spp. oocysts. The booster may comprise live oocysts from *Eimeria maxima* or any other Eimeria spp.

Furthermore, the booster may be given to the hens or the young chicks which comprises affinity purified native or recombinant Eimeria spp. antigenic protein, which includes all or substantially all of the Eimeria antigen (e.g. affinity purified 56 Kd, 82 Kd or 250 Kd *E. maxima* gametocyte antigens, a fusion protein derived from the 56 Kd, 82 Kd or 250 Kd *Eimeria maxima* gametocyte antigens, or the gene itself in a recombinant viral pox vector). The administration of the antigenic proteins may comprise intravenous, intramuscular or intraperitoneal injection of the affinity purified or fusion proteins, or by infection with live recombinant virus. Finally, the suitable time of administration is either prior to fertilization of the hen, or during the whole period of growth of the offspring chicks.

Alternatively, the booster may be given to the hens or young chick which comprises a combination of Eimeria spp.

affinity purified native or recombinant gametocyte antigens with recombinant antigens from the asexual (merozoite and sporozoite) stages of development.

Certain embodiments of this invention are exemplified in the Examples which follow. The Examples are set forth to aid in an understanding of the invention but are not intended to, and should not be construed to limit in any way the invention as set forth in the claims which follow.

Example 1

Purification of Eimeria maxima gametocytes

Two methods were employed in order to purify gametocytes from *E. maxima*. Method I was used in the early studies, however, it was found that these preparations were highly contaminated with host protein in spite of the fact that they looked fairly clean microscopically. Method II was far superior and resulted in gametocyte preparations which were greater than 90% pure. The methods are described below in detail.

Method I: Chickens were infected with 10,000 oocysts each and then sacrificed on day six post infection. Their intestines were cut open and the mucosa was scraped with glass slides into SAC buffer (170 mM NaCl, 10 mM Tris pH 7, 10 mM Glucose, 5 mM $CaCl_2$, 1 mM PMSF, 1 mg/ml bovine serum albumin). After quick blending for 10 seconds, the mixture was filtered through a series of polymon filters of pore sizes 150 microns down to 10 microns. The material that accumulated on the 10 micron filter was then washed, spun and examined microscopically. Using this method $10 \times 20 - 10^6$ gametocytes per intestine were obtained, however, as described above they were not as pure as those obtained by Method II.

Method II: Chickens (2–6 weeks) were infected as above. The optimal time for gametocyte production was determined to be 136–138 hours post infection. The chickens were then sacrificed, their intestines removed and washed with ice cold SAC. One end of the organ was tied with a string and the intestine was filled with 0.5 mg/ml hyaluronidase (Type III from Sigma, 700 units/mg (19)) in SAC. The other end was then tied and the intestines placed in warm 37° C. PBS in a beaker and subsequently incubated for 20 minutes at 37° C. with shaking. During this time the gametocytes were released from the intestine. After incubation the intestine was cut open and the contents discarded. The gametocytes were then washed off the intestinal mucosa with SAC through a 17 micron polymon filter (Swiss Silk Bolting Cloth Mfg. Co. Ltd., Zurich, Switzerland). The flowthrough was filtered through a 10 micron polymon filter and the gametocytes accumulating on the filter were washed with SAC and collected by centrifugation at 800×g for five minutes. They were then examined microscopically and counted in a modified Fuchs-Rosenthal counting chamber. The yield was $0.5-2 \times 10^6$ gametocytes per infected intestine, however, on a few occasions much higher yields of $10-20 \times 10^6$ gametocytes per infected bird were obtained. The reason for this is not clear and does not appear to be related to the intensity of the infection or the size of the birds.

Example 2

In vivo active immunization with purified *E. maxima* gametocytes

Experiments were carried out in order to test the purified *E. maxima* gametocytes as an immunogen in birds which were subsequently challenged with sporulated *E. maxima* oocysts. These data are summarized in four experiments:

Experiment 1: In this experiment one-day old chickens kept in one cage were immunized with $0.5-1.0 \times 10^6$ gametocytes prepared by Method I (half of which were sonicated in order to release internal components). Five birds received three weekly injections of gametocytes in Freund's adjuvant IM. Five received three weekly injections of Freund's adjuvant alone. Five received injections of gametocytes IV and five were not immunized and used as negative controls. One week after the last immunization, the birds were challenged per os with 2000 sporulated *E. maxima* oocysts (apart from the negative controls which were not challenged). Two day fecal samples were collected five days after infection and oocyst output was determined. As can be seen in Table 1 the five negative controls were all zero as expected. Birds given Freund's alone secreted an average of $26 \times 10^6$ oocysts/bird, birds immunized with gametocytes IV or IM actually produced by average more oocysts than the controls ($37 \times 10^6$/bird in both groups). From these results it was concluded that the antigen preparation used in this experiment showed an immunosuppressive effect on the ability of the chicks to resist infection. Similar results were found by others who tried immunizing with pure oocysts and, since the preparations used in the present experiments are contaminated with small numbers of oocysts, this may explain the effect.

When the gametocyte proteins were analyzed on SDS acrylamide gels it was found that this type of preparation (Method I) was highly contaminated with host proteins. In subsequent experiments much cleaner gametocytes were used prepared by Method II, older birds were used, since they are more immunocompetent, and the challenge dose was lowered to 500 oocysts/bird.

TABLE 1

| | (Experiment #1) | | | | | | |
|---|---|---|---|---|---|---|---|
| Treatment | Oocyst Challenge | Oocyst Output (millions/birds) | | | | | Average |
| Uninjected | 0 | 0 | 0 | 0 | 0 | 0 | 0 |
| Gametocytes intramuscular + Freund's complete adjuvant | 2,000 | 16 | 34 | 41 | 46 | 50 | 37.4 |
| Gametocytes intravenous | 2,000 | 4.7 | 31 | 35 | 55 | 60 | 37.4 |
| Buffer only + Freund's complete adjuvant | 2,000 | 6.2 | 13 | 19 | 33 | 58 | 25.8 |

Experiment 2: In this experiment, gametocytes (prepared by using Method II as described above) were used which were shown to contain little contaminating host protein by gel electrophoresis (see Example 3). $2 \times 10^6$ *E. maxima* gametocytes were injected into the duodenal loop of six week old birds twice at weekly intervals and one week later the birds were challenged with 500 *E. maxima* oocysts per os. Control birds were kept in the same cage as the immunized birds and oocyst output of all the birds was found to be zero prior to challenge. On days seven to nine after infection, feces were collected and oocyst output data are shown in Table 2. The control birds gave an average oocyst output of $52.2 \times 10^6$/bird while the immunized birds gave an average of $30.5 \times 10^6$ oocyst/bird. Three out of four of the immunized birds were much lower than the average control.

TABLE 2

(Experiment #2)

| Bird | Day 7 | Day 8 | Day 9 | Total oocyst output (× $10^6$) |
|---|---|---|---|---|
| 1 | 14 | 13 | 41 | 31 |
| 2 | 16 | 38 | 4 | 58 |
| 3 | 28 | 41 | 12 | 81 |
| 4 | 20 | 18 | 2 | 40 |
| 5 | 19 | 30 | 2 | 51 |
| Average oocyst output of controls = 52.2 × $10^6$ | | | | |
| 6 | 9 | 13 | 0 | 22 |
| 7 | 33 | 39 | 2 | 74 |
| 8 | 8 | 5 | 0 | 13 |
| 9 | 4 | 9 | 0 | 13 |
| Average oocyst output of immune = 30.5 × $10^6$ | | | | |

Experiment 3: In this experiment, three 5-week old birds were immunized IV and IP with three weekly injections of 1–2×$10^6$ *E. maxima* gametocytes. Three positive controls were kept in the same cage. One day after the last injection, birds were challenged with 500 oocysts per os. The results (Table 3) show that the three positive controls had an average two-day oocyst output of about 14×$10^6$/bird. One immunized bird did not secrete any oocysts, one bird showed a very high oocyst output and the other immunized bird was similar to the controls. In order to be certain that all the birds were indeed infected, all of the chickens were reinfected. The second infection showed that all the birds were immune including the "0" bird.

TABLE 3

(Experiment #3)

| Bird | Type | Oocyst output (× $10^6$) |
|---|---|---|
| 1 | Positive Control | 6.9 |
| 2 | Positive Control | 35 |
| 3 | Positive Control | 13.8 |
| 4 | Immunized | 43 |
| 5 | Immunized | 0 |
| 6 | Immunized | 12.3 |

Experiment 4: In this experiment birds were immunized with pure gametocytes, half of which were sonicated, given either IP, IM or IV. There were five positive controls. One day after the last immunization the birds were challenged with 500 oocysts and seven-ten days later feces were collected. As can be seen in Table 4, in the IP, IM group four out of seven birds showed a reduction down to 25% of the average control. In the IV group five out of seven birds were low. The average output of the groups showed the following: the IP, IM and IV groups were lower than the average control (36.7×$10^6$, 32.6×$10^6$, vs 55.6×$10^6$ respectively). Two control birds in this experiment were low and one of them was particularly low (#5). This bird had a broken wing which may have contributed to this result.

TABLE 4

(Experiment #4)

| Treatment | Bird # | Day 7 | Day 8 | Day 9 | Day 10 | Total oocyst output (× $10^6$) |
|---|---|---|---|---|---|---|
| Positive Controls | 1 | 2.0 | 45 | 45 | 1.1 | 93 |
|  | 2 | 2.3 | 44 | 23 | 5.0 | 74 |
|  | 3 | 5.1 | 52 | 26 | 2.0 | 85 |

TABLE 4-continued (Experiment #4)

| Treatment | Bird # | Day 7 | Day 8 | Day 9 | Day 10 | Total oocyst output (× $10^6$) |
|---|---|---|---|---|---|---|
|  | 4 | 0.6 | 5 | 11 | 1.5 | 18 |
|  | 5 | 0.3 | 1.3 | 4 | 2.2 | 8 |
| Average oocyst output control = 55.6 | | | | | | |
| Gametocyte IM-IP | 6 | 0.65 | 25 | 25 | 12 | 63 |
|  | 7 | 1.35 | 14 | 7 | 1 | 23 |
|  | 8 | 0.6 | 15 | 13 | 4.5 | 33 |
|  | 9 | 1.4 | 27 | 20 | 3.1 | 52 |
|  | 10 | 0.0 | 1.7 | 10 | 5.4 | 17 |
|  | 11 | 1.0 | 12 | 14 | 18 | 45 |
|  | 12 | 0 | 6 | 10 | 7.8 | 24 |
| Average oocyst output IM - IP = 36.7 | | | | | | |
| Gametocyte IV | 13 | 0.5 | 7 | 12 | 3.4 | 23 |
|  | 14 | 0.1 | 7.5 | 14 | 8.0 | 29 |
|  | 15 | 0.5 | 14 | 11 | 2.3 | 27 |
|  | 16 | 0.1 | 7 | 14 | 2.5 | 24 |
|  | 17 | 0.4 | 12 | 12 | 1.7 | 26 |
|  | 18 | 3.7 | 27 | 8 | 0.2 | 39 |
|  | 19 | 2.9 | 28 | 17 | 12.5 | 60 |
| Average oocyst output IV = 32.6 | | | | | | |

The experiments described above show that birds immunized with purified gametocytes injected IV, IP, IM or intraintestinally were partially protected against challenge infections. Preparations which were unclean (Experiment 1) seemed to have an immunosuppressive effect as has been reported previously using oocyst preparations to immunize chickens (26). Several of the sera from birds immunized in these experiments were analyzed for their titer and specificity as described below (Example 4). Both immune sera and sera from recovered birds (which was shown previously to confer a good level of protection when given passively) recognized the same antigens as determined by immune precipitation and Western blotting. Therefore, it was concluded that these antigens are protective and can be used to confer immunity to coccidial infections in chickens.

Example 3

Extraction of *E. maxima* gametocyte protein and RNA

Extraction of proteins from gametocytes prepared by Methods I and II (see Example 1) was carried out using various detergents. The yield of protein as determined by the method of Bradford (31) was 1–2 mg per 1×$10^6$ pure gametocytes. Extracted proteins were examined by SDS polyacrylamide gel electrophoresis (SDS-PAGE) and the efficiency of extraction using the various detergents was compared. It was found that by incubating gametocytes in a solution of 0.5% NP-40 in SAC at 4° C. for 1 hour, all of the protein extractable using the very strong detergent SDS was present in the solution (as determined by SDS-PAGE analysis). Results also showed that gametocytes prepared by Method I were heavily contaminated with host proteins, while in contrast, using Method II there was very little host contamination. This is based on both SDS-PAGE of Coomassie blue stained proteins as well as $^{35}$S-methionine metabolically labeled gametocyte proteins. The proteins had molecular weights between 10,000–300,000 daltons with 5 major metabolically labeled proteins of molecular weights of about 82 Kd, 73 Kd, 56 Kd, 52 Kd and 35 Kd (Table 5 and FIG. 1). Most of the major labeled bands seen in the gametocyte preparations were totally absent from the labeled uninfected control intestine, and the major bands seen in the uninfected control were either very weak or absent from the gametocyte protein preparation. Therefore, it was concluded that these proteins must be parasite derived and that the isolated parasites are metabolically active.

RNA was also extracted from *E. maxima* gametocytes using two procedures; one based on SDS-phenol (20) and one using guanidinium thiocyanate (21). The yields were 1–2 mg total RNA per $10^7$ gametocytes using either method. RNA from gametocytes, sporulated oocysts and uninfected chicken intestine were analyzed on 1.5% agarose gels where it was found that the rRNAs of *E. maxima* migrated differently from the host RNA. Based on the intensity of the ethidium bromide stained major rRNA bands, it was found that the gametocyte RNA preparations contained very little host RNA. In some preparations the host RNA contamination was negligible. These results corroborate those found at the protein level and indicate that the parasite preparations were greater than 90% pure.

Poly A containing mRNA was prepared from the gametocyte total RNA by oligo (dT)—cellulose chromatography (22). Gametocyte poly $A^+$mRNA and total RNA as well as uninfected control intestine RNA were translated in a rabbit reticulocyte cell-free system (23) where it was found that the gametocyte cell-free products contained little if any contaminating host cell-free products. There were eight major bands with molecular weights of about 34 Kd, 40 Kd, 45 Kd, 50 Kd, 65 Kd, 95 Kd, 100 Kd and 225 Kd, some of which were similar in size to the five major metabolically labeled gametocyte bands (35 Kd, 52 Kd, 56 Kd, 73 Kd, and 82 Kd) (see FIG. 1). The relationship of these bands was analyzed by immune precipitation an Western blotting as described in Example 4.

A time course experiment was performed by extracting RNA from infected mucosa every four hours starting on day five post infection with oocysts. These RNAs were translated in the rabbit reticulocyte cell-free system and compared to products directed by day six purified gametocyte RNA as well as control mucosa RNA. It appeared that various gametocyte bands were present at different times during development, however no major bands were detected early in gametocyte development which were absent from the mature gametocytes. It was concluded, therefore, that the preparations contained most if not all of the detectable gametocyte protein mRNAs.

Example 4

Characterization of protective antigens from *E. maxima* gametocytes

Several methods were employed in analyzing the antigens extracted from *E. maxima* gametocytes. These include (A) ELISA (enzyme linked immunosorbent assay), (B) immunofluorescence, (C) Western blotting, and (D) immune precipitation of cell-free translation products. The antisera employed in the studies were from chickens which recovered from *E. maxima* infections and were bled 14 days post infection (this type of sera was shown by Rose to be potentially protective in vivo (5–8) hereinafter "recovered sera"). The following groups were studied: chickens immunized with sonicated and whole pure gametocytes, mice immunized with sonicated and whole pure gametocytes, mice immunized with NP-40 extracts of pure gametocytes, and rabbits immunized with NP-40 extracts of pure gametocytes.

(A) ELISA

Animals were bled and the titer in the sera determined by ELISA (Table 5). Normal mouse sera and normal rabbit sera were found to be at background levels at a dilution of 1:50. Immune mice sera showed a positive titer up to a dilution of 1:1250 and immune rabbit sera were found to be positive up to 1:10,000, the highest dilution tested. We did, however, find a titer against host antigens and, therefore, a competition experiment was performed to determine whether the strong response found in immune rabbit sera was indeed against gametocyte antigen and not against host contaminants. The immune rabbit serum was preincubated with either gametocyte extract or normal chick intestine extract. Preincubated sera were then compared with untreated immune rabbit sera at a dilution of 1:1000. Sera preincubated with host material tested on chicken intestinal antigens reduced their activity to very low levels, while sera preincubated with gametocyte extract reduced their activity only partially. In contrast, the preincubation with gametocyte extract decreased the response against the parasite antigens close to background levels whereas the competition with host material on gametocyte antigens only lead to a slight decrease. We interpret this result to mean that rabbits, when immunized with gametocyte extracts, do respond to the host contaminants, nevertheless the major immune response is against the parasite. (Similar experiments were performed with both immune mice sera and recovered chicken sera, see Table 5). We have shown with the above experiments, that *E. maxima* gametocytes are immunogenic in both mice and rabbits. To shown that chickens, the natural host of *E. maxima*, also respond to gametocyte antigens, we analyzed sera of normal chickens and chickens which were infected with *E. maxima* and bled 14 days p.i. (recovered chicken sera). By using the ELISA technique normal chicken sera did not respond to the gametoycte antigens (Table 5). The majority of all recovered chicken sera tested showed titers of at least 1:1000 against gametocyte antigens with no response to control antigens. Chickens having an infection with *E. maxima* therefore clearly develop an immune response to the gametocyte stage of the parasite.

(B) Immunofluorescence

The immunofluorescence test was used to determine localization and stage specificity of the gametocyte antigens. Briefly, freshly prepared gametocytes were incubated with sera for 20 minutes at 37° C., washed 3 times with PBS, and then incubated with FITC conjugated second antibody. In control experiments where gametocytes were incubated with FITC conjugated rabbit anti-chicken IgG, rabbit anti-human IgG, rabbit anti-mouse IgG, or sheep anti-rabbit IgG (without antisera to the parasite present), a very high specific background was found even at dilutions as high as 1:1000. Noninfected chicken intestinal tissue did not react with any of the FITC-conjugates and reabsorption of these antibodies with either a chicken liver homogenate or purified gametocytes did not reduce this binding. In addition, preincubation with normal rabbit IgG did not affect the background.

In order to avoid the background problem, the $F(ab')_2$ fraction of affinity purified sheep anti-mouse IgG FITC conjugated (SIGMA, St. Louis, Mo.) was used as the fluorescent reagent. Control experiments indeed showed that this reagent by itself or with normal mouse serum gave a very low background. This result indicates that the background found with IgG may be due to the presence of Fc receptors on the surface of the gametocytes.

Thirteen immune mouse sera were then tested from mice immunized with either whole plus sonicated gametocytes or gametocyte NP-40 extracts. It was found that the various immune sera showed different intensities in their response with no significant difference between sera against whole gametocytes or gametocyte NP-40 extracts. In all instances the fluorescence was concentrated on the surface of the gametocytes indicating that the antigens are surface membrane associated. Some of the sera also reacted with the surface of oocysts.

The stage specificity of the mouse anti-gametocyte sera was also tested. *E. maxima* sporozoites were isolated according to published procedures (22) and were dried on IFA glass slides. The immunofluorescence assay was carried out where it was found that the sporozoites fluoresced with a few sera, however not nearly with the intensity seen with purified gametocytes. Therefore, it was concluded that there may be some antigens present in both sporozoites and gametocytes which cross-react, however, the bulk of these proteins are present mainly in gametocytes.

(C) Western blotting

Identification of the individual antigens recognized by immune and recovered sera was performed by immunodetection of immobilized antigens (Western blotting (25)) and by immune precipitation of the cell-free synthesized gametocyte proteins. NP-40 extracted gametocyte proteins were first separated by SDS-PAGE and then transferred to a nitrocellulose filter. Immunodetection was performed either with $^{125}$I-protein A (25) or with the horseradish peroxidase method (25). Results with $^{125}$I-protein A are presented in FIG. 2 and with the horseradish peroxidase method in FIGS. 3A, 3B, 3C, and 3D and are summarized in Table 6.

Figure 2:
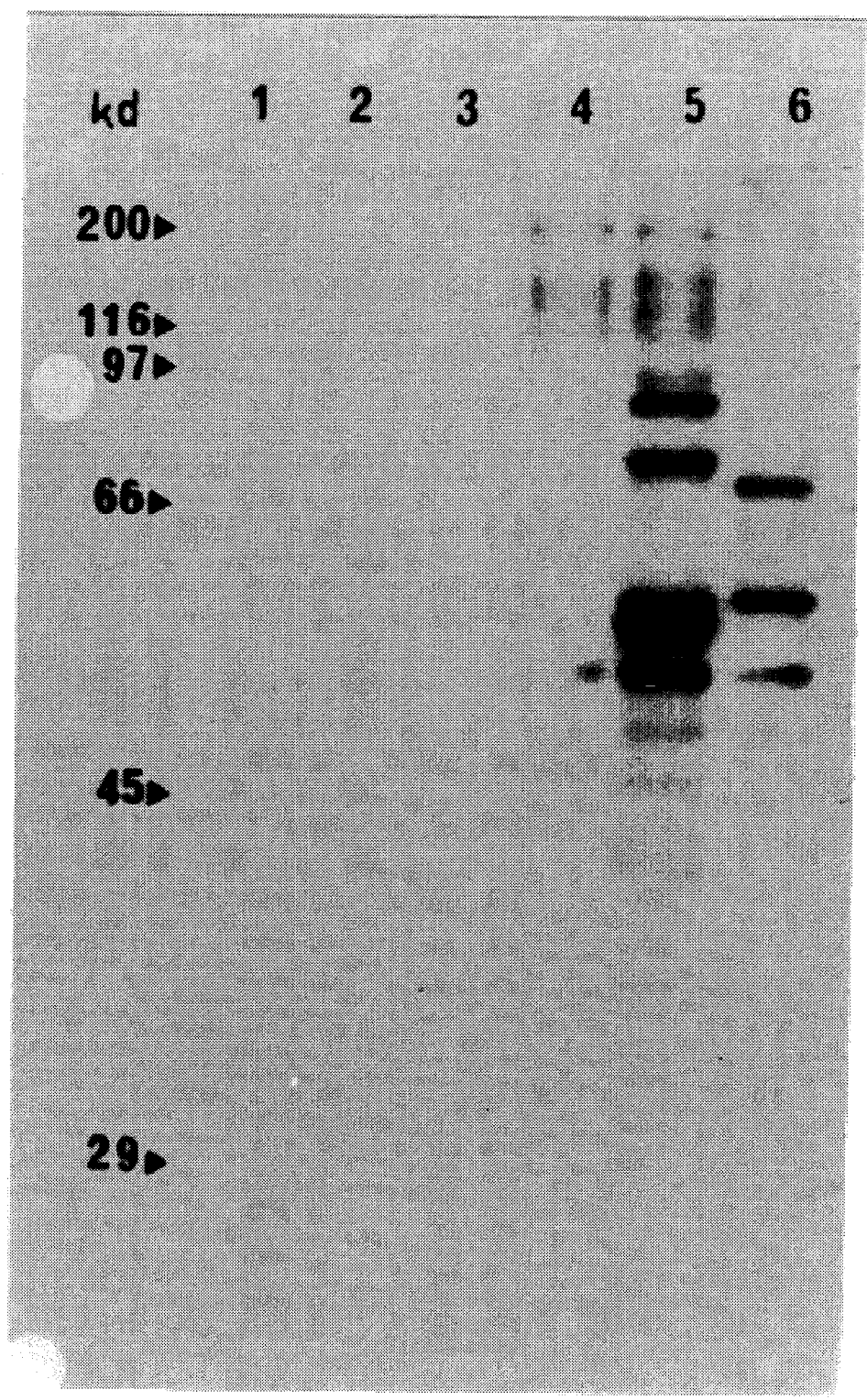
FIG. 2 depicts the immunodetection of gametocyte and control proteins with rabbit antigametocyte NP-40 extract serum. Gametocyte and host tissue proteins were blotted on to nitrocellulose paper and reacted with normal rabbit serum (Lanes 1,2,3) or serum from rabbits immunized with gametocyte NP-40 extracts (Lanes 4,5,6). Host tissue protein extract (Lanes 1,4) is hardly reactive compared with gametocyte protein extracts (Lanes 2,3,5,6).

It was found that normal rabbit sera reacted very weakly with only a few bands in both control and gametocyte antigen preparations. In contrast, the rabbit anti-NP-40 gametocyte extract sera strongly reacted with bands in the gametocyte protein extract and weakly with control intestine protein extracts. Although some variability exists between different protein extracts, rabbit anti-gametocyte extract serum consistently detected 6 major (90 Kd, 82 Kd, 75 Kd, 73 Kd, 58 Kd and 56 Kd) and 6 minor (94 Kd, 48 Kd, 45 Kd, 41 Kd, 39 Kd and 34 Kd) gametocyte specific proteins (FIG. 2).

Mice were immunized with 3 injections of NP-40 extracts of purified *E. maxima* gametocytes (1–2 mg protein/injection based on the Bradford assay (9)) at 1–2 week intervals and were bled 1 week after the final boost. Mouse antigametocyte sera reacted strongly with 2 proteins having molecular weights of 56 Kd and 82 Kd, whereas they hardly reacted with proteins extracted from control uninfected intestine. Preincubation of immune sera with uninfected intestine detergent extract had no effect on the intensity of the bands seen in the gametocyte extract, while preincubation of sera with gametocyte detergent extract greatly reduced the intensity of the bands. Normal mouse sera and normal rabbit sera did not react with either gametocyte or control intestine extracts. It was rather surprising to find no reactivity to control intestine proteins in spite of the presence of several host proteins in our gametocyte extract. Furthermore, these 2 major immune-detectable bands do not correspond with any major amido black stained proteins. These results show that the 56 Kd and 82 Kd molecular weight proteins are highly immunogenic even when injected as a minor component of a crude gametocyte extract.

Figure 3A:
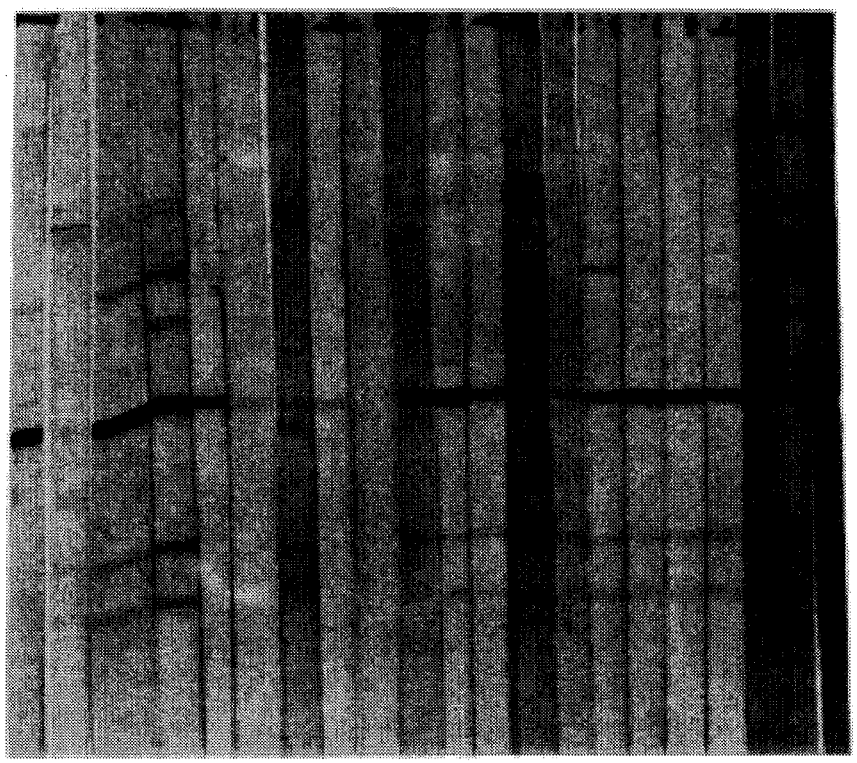
FIGS. 3A–3D depicts the immunodetection of gametocyte antigens with recovered chicken serum and normal chicken serum.
Figure 3B:
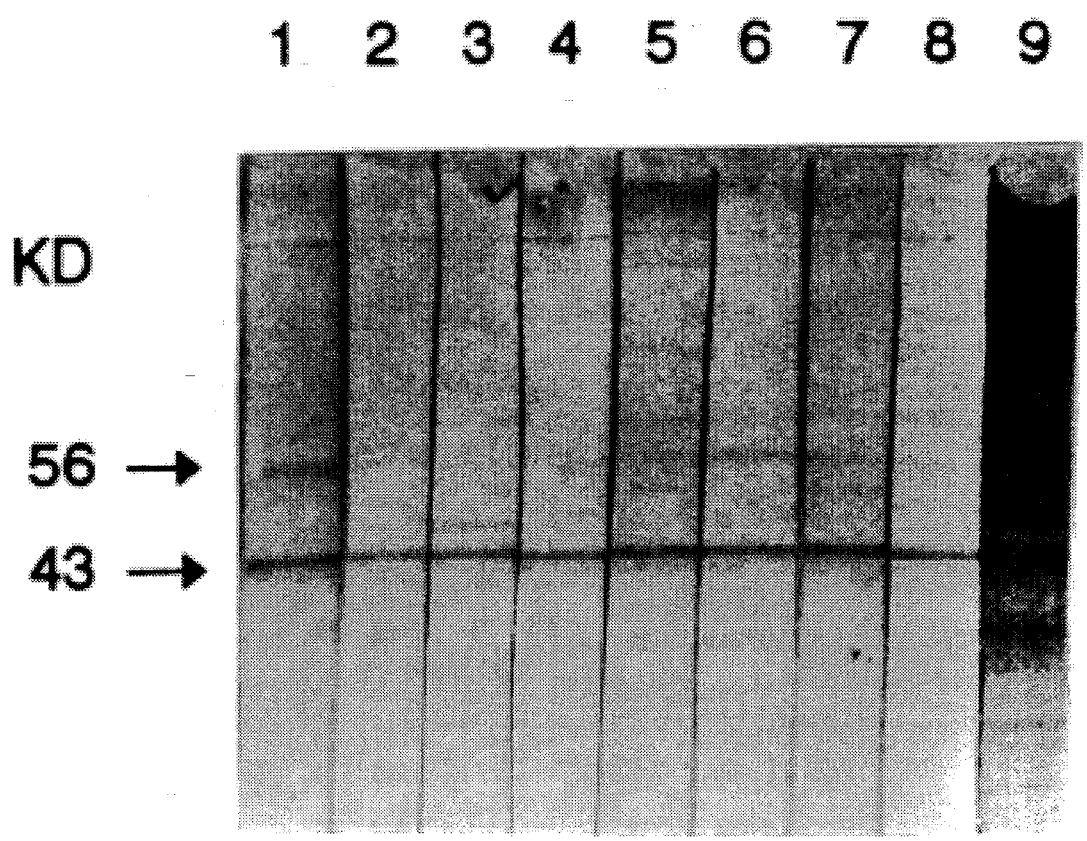

Using several recovered chicken sera we consistently detected 3 major bands having apparent molecular weights of 82 Kd, 56 Kd and 43 Kd regardless of the detergent used to extract the gametocyte protein (FIG. 3A). In contrast, normal chicken serum reacted mainly with the 43 Kd protein and much more inconsistently with the other 2 major bands (FIG. 3B). Uninfected control intestine proteins did not react at all with either recovered or normal chicken sera. In addition to the 3 major bands described above 6 minor bands were detected (250 Kd, 116 Kd, 78 Kd, 52 Kd, and 36 Kd) which appeared less consistently. These results are summarized in Table 6. Comparing rabbit antigametocyte sera and recovered chicken sera on the same blot, we found that the major bands recognized by both sera comigrated. Therefore, it was concluded that these two antigens are very immunogenic both in the course of an infection and when injected as a minor component of a crude gametocyte detergent extract in animals.

The reactivity of normal chicken sera with the 43 Kd protein can be explained in two possible ways. Either the sera contain a certain level of antibody against this gametocyte protein even though the chickens were never exposed to *E. maxima*, or the 43 Kd protein binds chicken Ig irrespective of its source. That the latter possibility is correct was shown by using affinity purified chicken anti-cytochrome Ig on a Western blot where it was found that it also bound to the 43 Kd protein band. Thus, it was concluded that the 43 Kd protein is and Ig binding protein, and may in fact be the Fc receptor responsible for the binding of Ig seen in the immunoflorescence studies (see above part B).

Figure 3C:
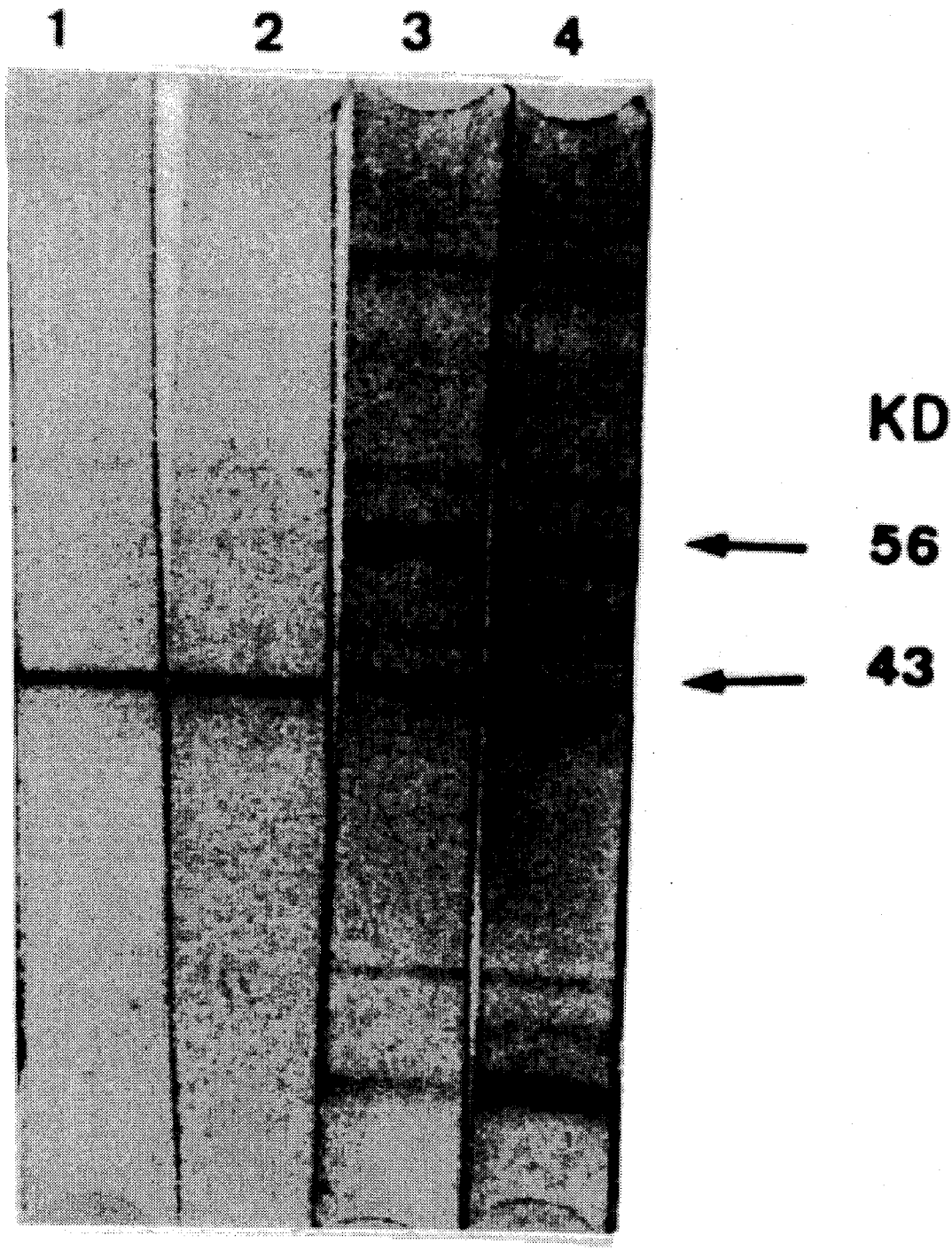

An experiment was performed to determine on which day post-infection antibodies to the major gametocyte protein bands appear in vivo. Chickens were inoculated per os with 10,000 *E. maxima* oocysts on day 0 and were bled on days 0, 6, 11 and 14. It was found that on days 0 and 6 the only major band visible was the 43 Kd protein, whereas sera taken on days 11 and 14 reacted strongly with the 56 Kd protein (FIG. 3C).

Since it was reported by Rose (5), that sera taken prior to day 10 post-infection give, no protection by passive immunization against challenge infections in naive birds, while day 14 sera give good protection, our results indicate that the 56 Kd protein plays an important role in protective immunity.

Figure 3D:
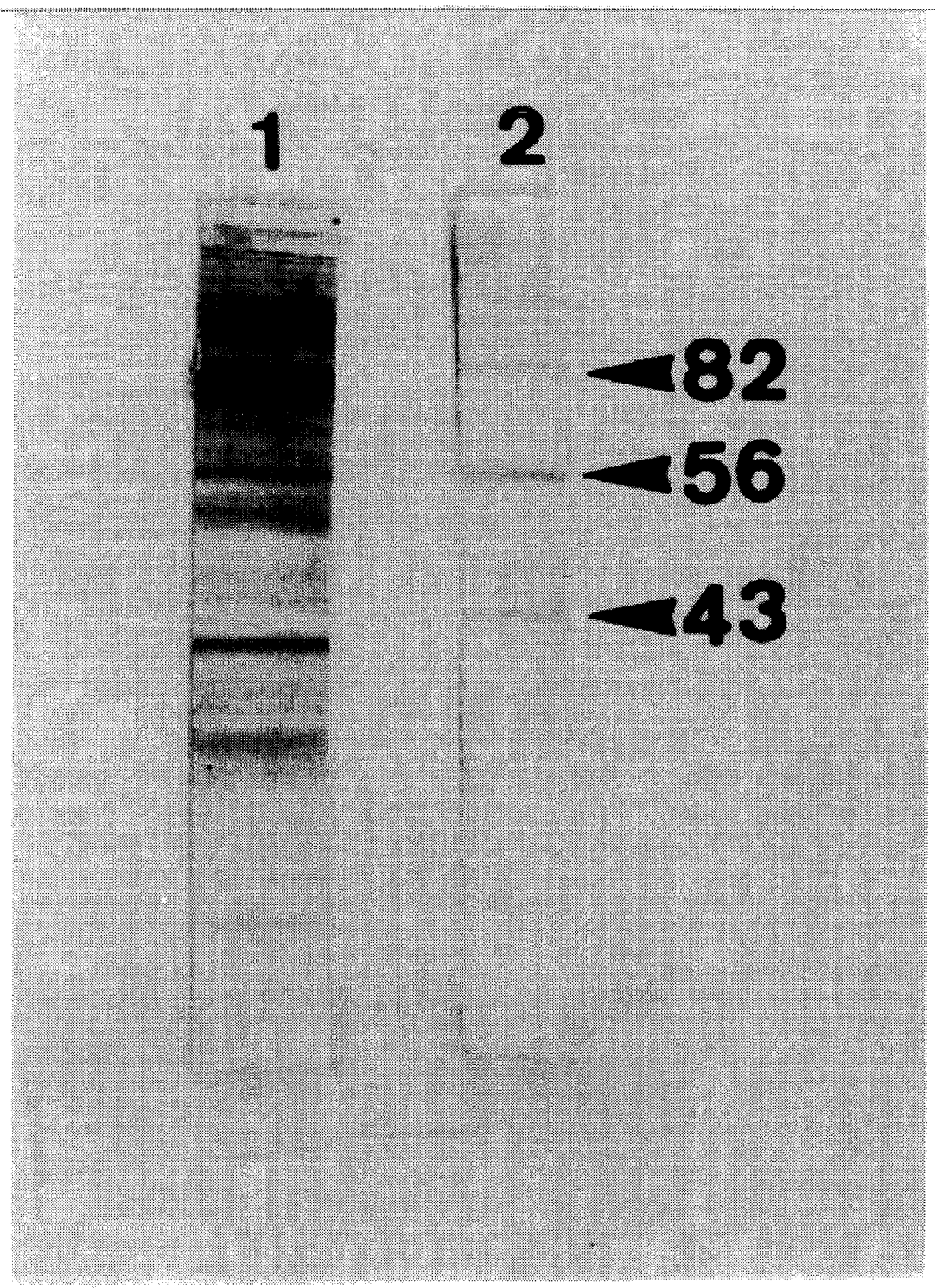

In previous reports maternal antibody was mentioned as playing an important role in resistance to coccidial infection in newborn chicks (4). However, the means by which this immunity is effected is unclear. We therefore tested whether or not newborn chick sera (i.e. a few hours post-hatching) contain a significant amount of maternal antibody to *E. maxima* gametocyte antigens. Using the ELISA technique we found that at a dilution of 1:500, 6 out of 6 newborn chick sera tested gave a very strong response to gametocyte antigens. In contrast, 25 sera taken from 10 day old chickens showed little or no reactivity at this dilution. Therefore, it was concluded that antigametocyte antibody is present in newborn chicks and its titer is greatly diminished by the age of 10 days. Using the Western blotting technique we found that most of the newborn chicken sera reacted with gametocyte antigens (FIG. 3D). Once again, the 56 Kd and 82 Kd molecular weight proteins are the predominant bands seen on the blots. For comparison, sera taken from 10 day old birds showed reactivity only with the 43 Kd molecular weight protein as expected for normal chicken serum (see above). These results corroborated those described above using the ELISA method, and show that antibodies to *E. maxima* gametocyte antigens are present in newborn chickens.

(D) Immune Precipitation of Cell-free Translation Products.

Figure 4:
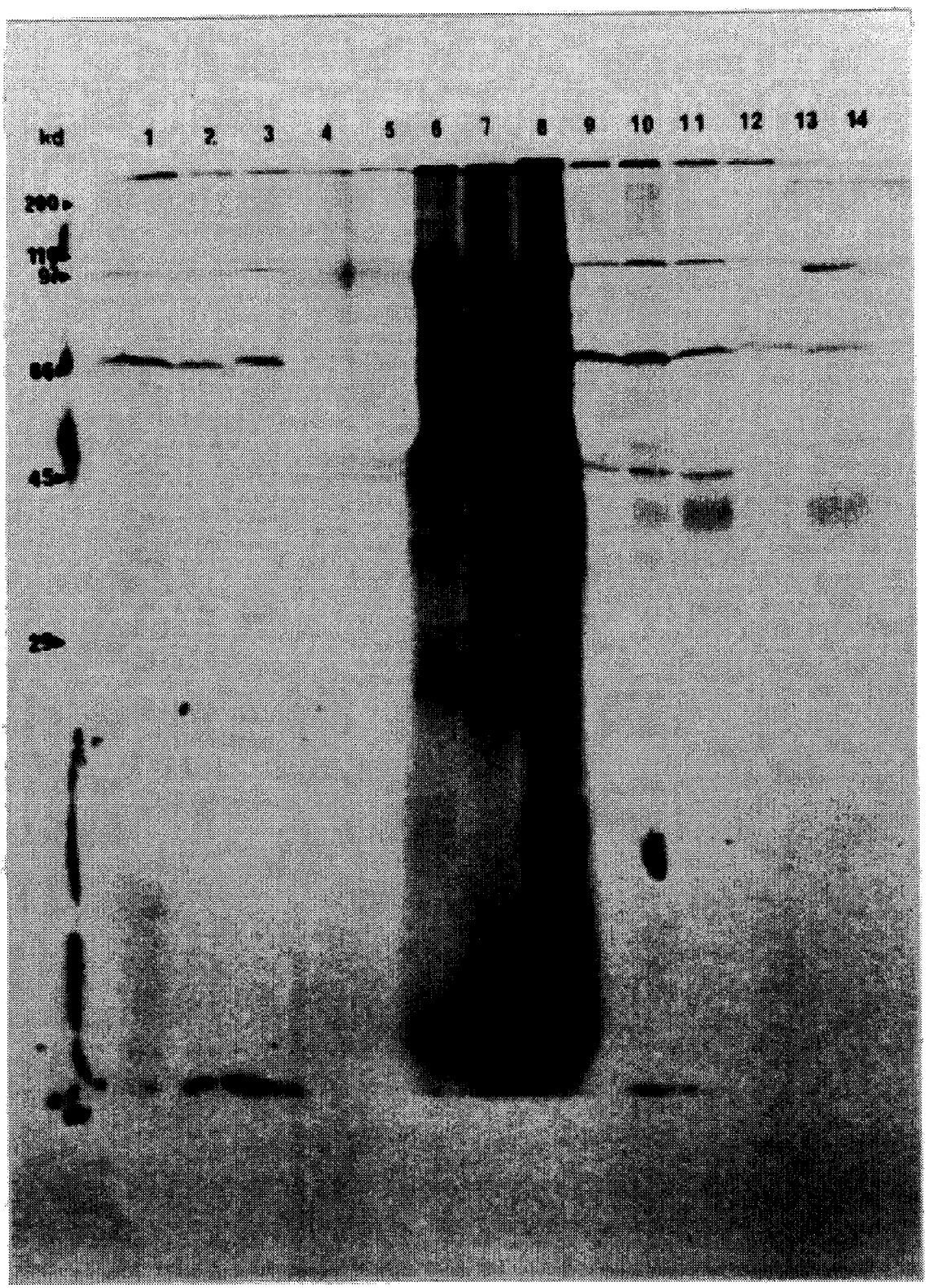
FIG. 4 depicts the immune precipitation of $E.$ $maxima$ cell-free proteins with rabbit and chick antisera. Cell free translation products of total sporulated $E.$ $maxima$ oocyst RNA (Lane 6), purified gametocyte RNA (Lane 8) and uninfected chick intestine RNA (Lane 7) were reacted with chick and rabbit antisera. Gametocyte cell-free proteins were immunoprecipitated with recovered chick serum (Lanes 9,10), chick antigametocyte NP-40 extract serum (Lane 11), normal chick sera (Lanes 1–3, 12), rabbit antigametocyte extract serum (Lane 13) and normal rabbit serum (Lane 14). Sporulated oocyst cell-free proteins were immunoprecipitated with recovered chick serum (Lane 4) and normal chick serum (Lane 5).

Antisera were used to identify antigens synthesized in vitro from gametocyte messenger RNA. mRNA was extracted by the guanidinium thiocyanate method (21) and translated in the rabbit reticulocyte cell free system (BRL, Bethesda, Md.). Cell-free products were immune precipitated with the various antisera and the proteins analyzed by SDS-PAGE (FIG. 4). It was found that antisera to gametocytes from a variety of immunized animals reacted with gametocyte directed cell-free products and not with cell-free products from uninfected intestine, merozoite stage infected intestine, sporulated oocysts, or chick brain. Recovered and immune chick sera recognized several gametocyte cell-free translation products. Long exposures of the autoradiographs showed more than ten immune precipitable bands having molecular weights from about 34 Kd-100 Kd. Of the ten bands, seven bands are prominent representing proteins, having molecular weights of about 100 Kd, 95 Kd, 65 Kd, 50 Kd, 40 Kd and 34 Kd, respectively (Table 6 and FIG. 4). These bands correspond to most of the major bands in the total cell-free products. Some of the sera recognized only the 100 Kd protein, others only the 95 Kd protein, while still others precipitated both bands. In all cases, the 45 Kd and 65 Kd proteins were immune precipitated.

Serum from animals immunized with NP-40 extracts precipitated the same bands apart from some variations. Rabbit anti-NP-40 extract clearly precipitated at 225 Kd protein along with the 95 Kd and 65 Kd and 45 Kd proteins, while the other bands were very weak. Mouse anti-NP-40 extract gave similar results, whereas those immunized with whole and sonicated gametocytes recognized two additional low molecular weight bands at about 10 Kd-20 Kd.

Figure 5:
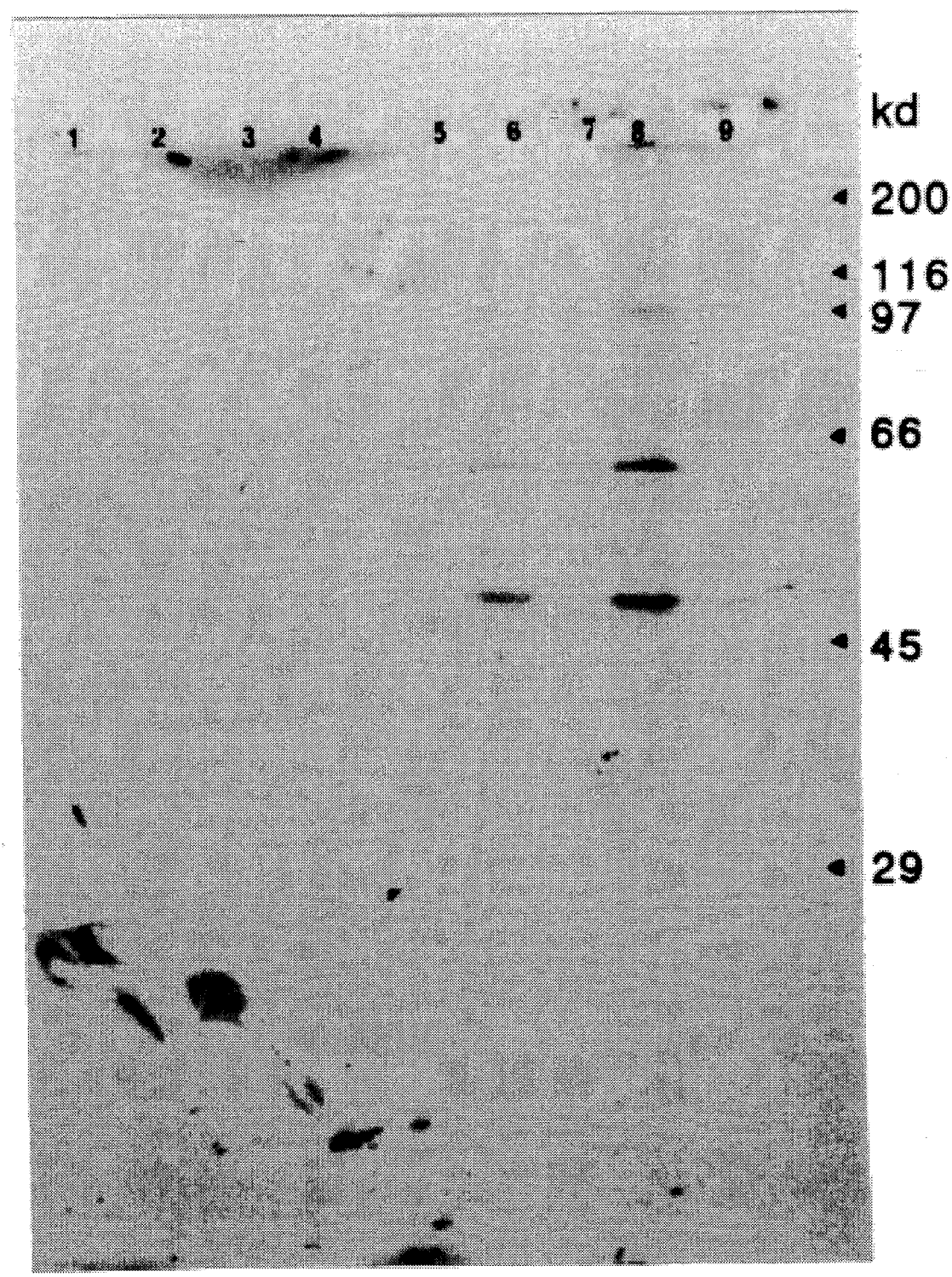
FIG. 5 depicts the immune precipitation of gametocyte cell-free products directed by mRNA of infected intestine extracted at various time points as compared to pure merozoite or gametocyte preparations. Gametocyte specific products derived from cell-free translation of total intestinal mRNA extracted during merozoite and gametocyte stages of $E.$ $maxima$ infections were immuneprecipitated with recovered chick serum. Immune-precipitates of cell-free translation of mRNA from: merozoites (Lane 1), infected intestine at 118 h (Lane 2), 122 h (Lane 3), 126 h (Lane 4), 130 h (Lane 5), 134 h (Lane 6) and 138 h (Lane 7) post infection with $E.$ $maxima$; purified $E.$ $maxima$ gametocytes (Lane 8) and chick brain (Lane 9).

When recovered chicken serum was reacted with cell-free translation products of total infected chick intestine RNA (taken at various times post infection) the proteins immune precipitated corresponded to those seen in pure gametocyte cell-free products (FIG. 5). Antigenic proteins started to appear at about 130 hours (approximately eight hours prior to the peak of gametocyte production in vivo 138 hours), labeled most strongly at 134 hours, and then decreased in intensity at 138 hours. Thus, the entire range of mRNAs encoding antigens stimulating the immune response during an infection with *E. maxima* are absent from the merozoite stage (96 hours) and are first detectable only at the late gametocyte stage. In addition, it would appear that none of these antigens are shared with the earlier developmental stages. The decrease in antigens precipitated with recovered chicken sera at 138 hours may reflect the transition of mature macrogametocytes to oocysts.

Table 6 summarizes the results described above. Gametocyte specific proteins show a characteristic pattern of 5 (metabolic labeling) or 8 (cell-free products) major bands. Of these, most are the same size as the major antigenic proteins recognized by immune precipitation or Western blotting with anti-gametocyte or recovered sera. As defined by the Western blotting technique there are three major antigens recognized by recovered chicken serum having apparent molecular weights of 82 Kd, 56 Kd and 43 Kd. One of these (56 Kd) also reacted strongly with immune rabbit serum and based on the time course experiment using post-infection-sera (FIG. 3) plays an important role in protective immunity. The 43 Kd protein appears to be an IgG binding protein and is likely to be an Fc receptor (as discussed above).

Using recovered chicken serum to immune precipitate cell-free translation products, we also found 3 major bands which appear consistently, having apparent molecular weights of 100 Kd, 65 Kd, and 45 Kd (see FIGS. 4 and 5). These three bands correspond to the three major bands seen on the Western blots. (See Example 7) Normal mouse serum and normal rabbit serum reacted with the 65 Kd protein in cell-free translation products. The same protein reacted with affinity purified chicken anti-cytochrome C antibodies, showing that this is also an Ig binding protein which may be homologous to the 43 Kd protein seen on Western blots. It is interesting to note, that normal chicken serum from uninfected birds both in the laboratory and from the field reacted consistently with the 100 Kd and 65 Kd proteins in cell-free translation products (FIG. 4) as well as (although less consistently) with the 82 Kd and 56 Kd proteins on Western blots (FIG. 3). These results indicate that these antigens are highly conserved between various species of coccidia. Additional evidence for this is provided by the fact that sera from chickens which were recovered from infections by other Eimeria species also react to these three major antigens.

TABLE 5

Summary of ELISA results on gametocyte antigen

| dilution | 1:50 | 1:1000 | 1:1000 preinc. with gemetoctye | 1:1000 preinc. with control tissue |
|---|---|---|---|---|
| normal mouse sera | — | — | — | — |
| immune mouse sera | ++++ | ++++ | +/− | ++++ |
| normal rabbit sera | — | — | — | — |
| immune rabbit sera | ++++ | ++++ | +/− | +++ |
| normal chick sera | — | — | — | — |
| recov. chick sera | ++++ | +++ | +/− | +++ |

TABLE 6

| Total metabolically labeled proteins | Total cell-free translation products | Immune precipitation from cell-free products with recovered chicken serum | Western blotting with recovered chicken serum | Soybean lectin on western blots | Immune precipitation from cell-free products with rabbit serum | Western blotting with rabbit serum |
|---|---|---|---|---|---|---|
|  | 225 ± 20 |  | 250 ± 20 |  |  |  |
|  | 100 ± 10 | 100 ± 10* |  |  | 225 ± 20 |  |
|  | 95 ± 10 | 95 ± 10 | 116 ± 10 |  |  |  |
| 82 ± 10 |  |  |  |  |  | 94 ± 10 |
|  |  |  |  |  | 95 ± 10 | 90 ± 10 |
| 73 ± 5 |  |  | 82 ± 10* | 82 ± 10* |  | 82 ± 10 |
|  | 65 ± 5 | 65 ± 5* | 78 ± 5 | 78 ± 5 |  |  |
| 56 ± 5 |  |  |  |  |  | 75 ± 5 |

TABLE 6-continued

| Total metabolically labeled proteins | Total cell-free translation products | Immune precipitation from cell-free products with recovered chicken serum | Western blotting with recovered chicken serum | Soybean lectin on western blots | Immune precipitation from cell-free products with rabbit serum | Western blotting with rabbit serum |
|---|---|---|---|---|---|---|
| 52 ± 5 | | | | | | 73 ± 5 |
|  | 50 ± 5 | 50 ± 5 | | | 65 ± 5 | 58 ± 5 |
|  |  |  | 56 ± 5* | 56 ± 5* | | 56* ± 5 |
|  | 45 ± 5 | 45 ± 5* | 54 ± 5 | 54 ± 5 | | |
|  |  |  | 52 ± 5 | 52 ± 5 | | |
|  | 40 ± 5 | 40 ± 5 | | | | 48 ± 5 |
| 35 ± 5 | 34 ± 5 | 34 ± 5 | | | 45 ± 5 | 45 ± 5 |
|  |  |  | 43 ± 5* | 40 ± 5 | | 41 ± 5 |
|  |  |  | 36 ± 5 | | | 39 ± 5 |
|  |  |  |  |  |  | 34 ± 5 |

*indicate major bands reactive with recovered chicken sera or soybean lectin

Example 5

Identification of gametocyte antigens by lectins

Lectins are proteins, found mainly in plants, which bind very specifically to receptors on cell surfaces. More accurately, they bind to distinct sugar moieties of the receptors. Most lectins interact preferentially with a single sugar structure on cell surfaces. This interaction with cells is so selective that lectins can be used to distinguish e.g. between different human blood groups (32). This specificity of lectins was used to test gametocytes for surface antigen binding.

To facilitate the analysis, several commercially available lectins, all conjugated to fluorescein, were checked, namely wheatgerm lectin (Triticumvulgare), soybean lectin (Glycin max) and concanavalin A (all Bio-Makor, Rehovot). The lectins were each incubated for 35 minutes at room temperature with 50,000 gametocytes in 100 µl PBS at a concentration, for each lectin, of $10^{-2}$ µg/µl. After repeated washes with PBS the gametocytes were mounted on slides in PBS:Glycerol 1:1, and analyzed by fluorescence microscopy for surface binding to the lectins. Neither with wheatgerm lectin nor with concanavalin A could any specific binding be detected, i.e. both gametocytes and cell debris fluoresced to the same extent. Soybean lectin, however, bound very specifically to the surface of gametocytes only.

The specific sugar recognized by soybean lectin, N-acetyl-D-galactosamine (32), should inhibit the binding, if indeed the interaction observed is a true lectin-cell receptor reaction. In a competition experiment using this sugar at a concentration of 100 mM, the binding of soybean lectin could be completely inhibited. As expected for true lectin binding the inhibition was reversible. This result shows clearly, that some of the gametocyte surface moieties are indeed glycosylated.

In order to determine whether or not these surface moieties are glycoproteins and to relate them to the antigens detected by immune sera (see Example 4), lectin blots were used. The principle of lectin blots is similar to Western blots, however the lectin is allowed to react directly with the immobilized antigens without prior antiserum incubation. Lyophilized $Na_2$-DOC-extracts of gametocyte antigens and normal chicken intestines (see Example 6) were dissolved in water at a concentration of 10 mg/ml each. The antigens were separated on SDS-PAGE and blotted electrophoretically onto nitrocellulose paper. The paper was then cut into equal strips and tested for binding to soybean lectin. In order to visualize reactive glycoprotein bands, soybean lectin conjugated to peroxidase was used (Sigma, St. Louis).

The nitrocellulose strips were incubated in blocking solution (TBS pH 7.0, 10% FCS) for 10 minutes, then transferred to trays containing in addition to blocking solution, 5 mM $MnCl_2$, 5 mM $CaCl_2$ and 10 µg/ml soybean lectin-peroxidase; the strips were incubated for 1 hour at room-temperature. Control strips were treated as above, but all solutions contained in addition 100 mM N-acetyl-D-galactosamine. Negative controls consisted of nitrocellulose blots with immobilized normal chicken intestinal proteins.

After incubation the strips were washed extensively with TBS or TBS+sugar respectively. Binding was detected by incubating the strips in a solution containing a substrate that upon conversion by peroxidase gives rise to a color reaction.

Figure 6:
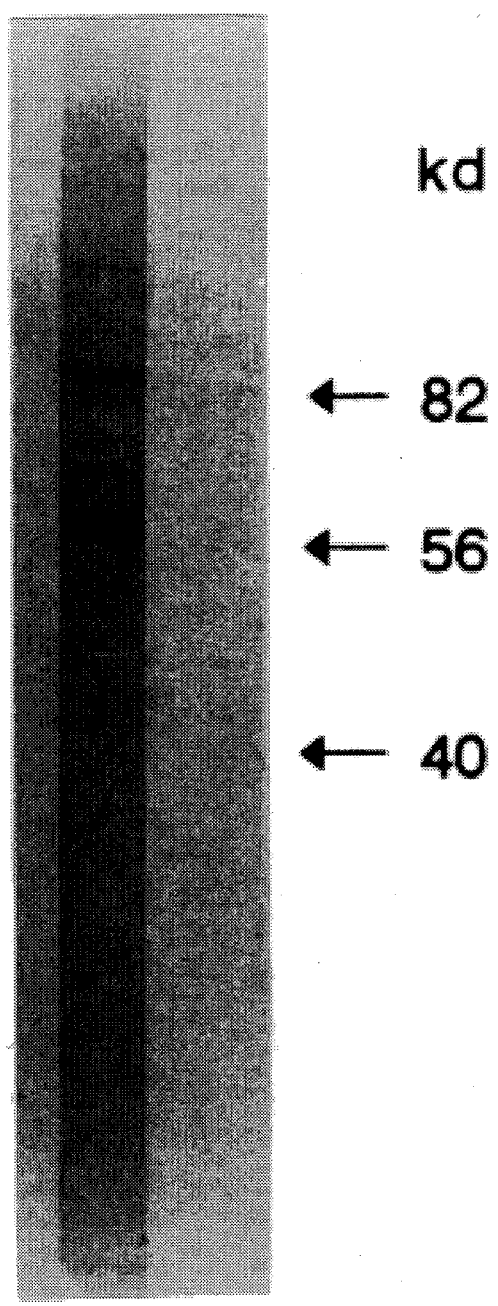
FIG. 6 presents a Western Blot of gametocyte proteins detected by soybean lectin conjugated to peroxidase. The most prominent proteins as depicted are those having molecular weights of 82 Kd, 56 Kd and 40 Kd.

By lectin blot analysis the normal chicken intestinal proteins did not react with soybean lectin. The gametocyte antigens, however, contain 10 bands, 5 major and 5 minor, which can be detected with soybean lectin. The major bands have apparent molecular weights of 82, 78, 56, 54 and 52 Kd all of which are identical in size to the major bands detected by recovered chicken serum in Western blots (see FIG. 6 and Table 6). As already expected from the immunofluorescence studies above, the sugar inhibited the soybean lectin binding completely, proving that the binding is indeed lectin specific. With the help of soybean lectin we have hereby clearly identified some of the major antigens of E. maxima gametocytes as being surface specific glycoproteins. The isolation of these proteins can easily be achieved by soybean lectin agarose column chromatography. To this purpose, 1 mg gametocyte NP40 extract in 200 µl TBS were incubated with 50 µl soybean lectin bound to agarose (SBL-A, Bio-Makor, Rehovot), for 90 minutes at 4° C., under constant shaking. During the incubation period, the glycoproteins bound to the soybean lectin. The SBL-A was then spun for 1 minute in a minicentrifuge and the nonbound material was removed. After 3 washes with 500 µl TBS, the gametocyte glycoproteins were eluted from the matrix by incubating the SBL-A-gametocyte complex with 50 µl of 100 mM N-acetyl-D-galactosamine (Sigma, St. Louis) in TBS. Elution was carried out at room temperature by shaking the tubes for 30 minutes. The SBL-A was again spun for 1 minute; the eluted material was then dialyzed against 10 mM phosphate pH 7.0, 1 mM PMSF, lyophilized and analyzed for its activity on Western blots as described before.

It was found that the eluted material reacted strongly with soybean lectin giving two major bands of 56 Kd and 82 Kd as expected. In addition, these two glycoproteins reacted strongly with recovered chicken serum and the 56 Kd protein also was recognized by monoclonal antibody 1E11-11 (Example 7). These results show that soybean lectin agarose can be used to affinity purify the 82 Kd and 56 Kd antigens, which can be used to carry out active immunization experiments in order to directly assess their role in protective immunity (See Example 12).

EXAMPLE 6

Storage and fractionation of E. maxima gametocyte antigens

Figure 7:
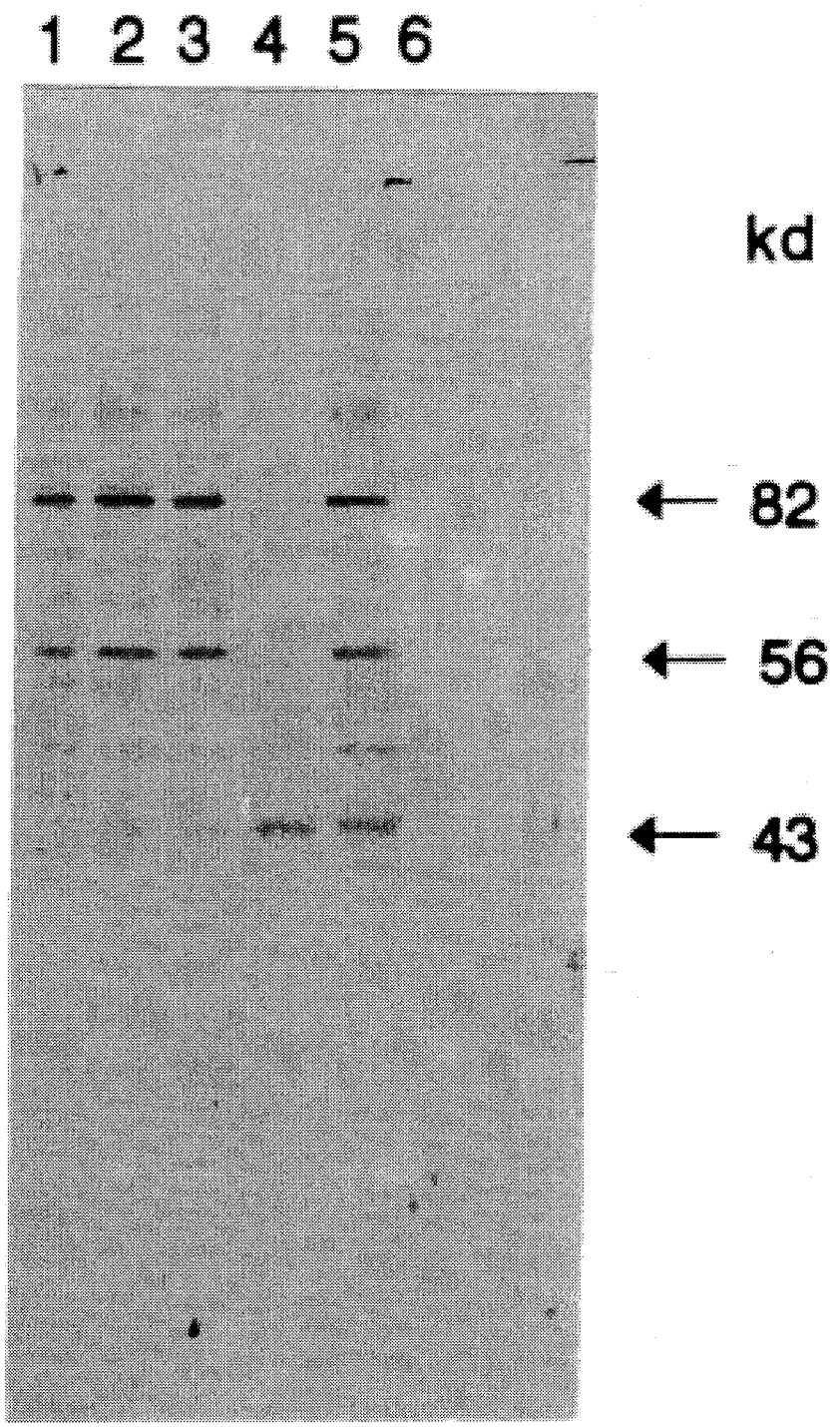
FIG. 7 presents extracts of gametocytes using a variety of detergents. The same number of gametocytes were extracted with 0.5% CHAPS (3'- [(3'-cholamidopropyl) dimethylammonio]- 1-propanesulfonate) (Lane 1), 0.5% NP-40 (Lane 2), 0.5% TRITON X-100 (Lane 3), 0.5% SDS (Lane 4) and 0.5% $Na_2$ DOC (Lane 5) were blotted on to nitrocellulose paper and reacted with recovered chicken serum.
Figure 7:
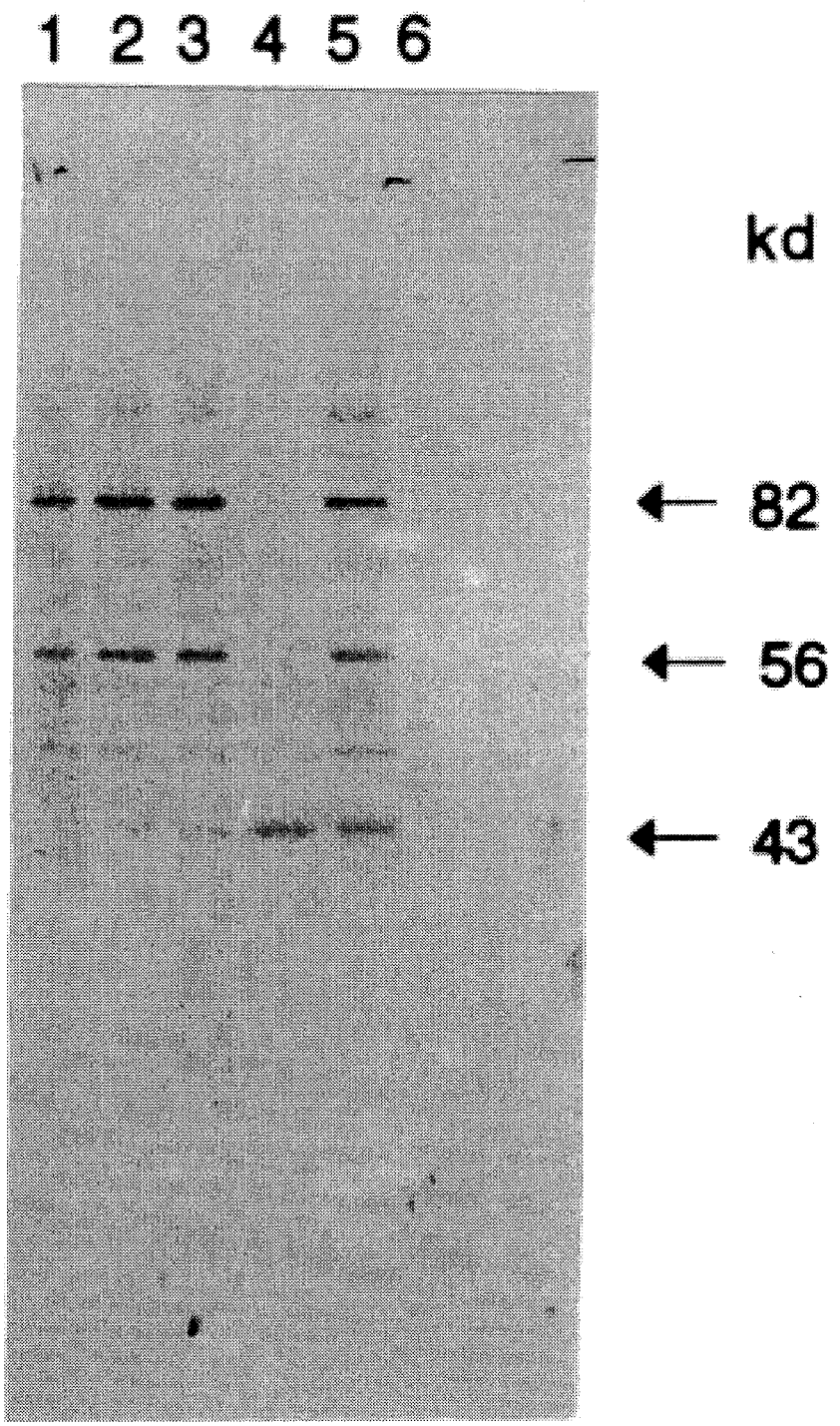

One of the most commonly used methods to store proteins is the freeze-drying or lyophilization technique. Freeze dried material can usually be stored for long periods of time without losing activity. Gametocytes purified according to method II (see Example 1) were extracted with a variety of detergents. The extracts were analyzed by Western blotting using recovered chicken serum, where it was found that extraction with Na$_2$DOC gave the best results (see FIG. 7). Consequently, large scale extraction was performed using Na$_2$DOC. The extract was subsequently dialyzed against a 10 mM phosphate buffer pH 8.0 containing PMSF at 4° C. The dialyzed material was frozen at −80° C. and then lyophilized to dryness. The antigens are stored with dessicant at −20° C. Western blots of the lyophilized material when developed with recovered chick serum, showed that all antigenic proteins were retained. In a comparison of ELISA from fresh material and freeze dried antigen no difference was found. It was concluded therefore that the best way to store total gametocyte antigen is in the form of a freeze dried powder.

Gametocyte extracts contain a mixture of proteins, lipids a.s.o. In order to separate the different components, but also at the same time fractionate the various antigens, we employed the technique of column chromatography as described below.

Pure gametocytes were extracted with 0.5% NP-40 (see Example 3). Proteins were precipitated by adding ammonium sulphate to the extract to a concentration of 10%. The precipitate was removed and the supernatant was brought to an ammonium sulphate concentration of 50%. The precipitated proteins (50%-cut) were tested in both ELISA and Western blots and shown to retain their activity. For column chromatography the 50% cut was dissolved in the column running buffer, namely: 10 mM Tris pH 8.0, 150 mM NaCl, 1 mM PMSF, 0.05% DOC and 1 mM EDTA.

Two different column media were used; both are separating on the principle of size fractionation, namely Sephadex G-200 and Sephacryl S-300 (both Pharmacia, Finland). The same column running buffer (see above) was used for either column. The fractionation achieved was in both cases very similar, i.e., the material separated into two major peaks. The gametocyte proteins active in ELISA and Western blots were shown to be concentrated on the descending slope of the first peak and in the trough between peaks. Antigen containing fractions were pooled, dialyzed and either used immediately or stored for short terms at 4° C. For long term storage the fractions were lyophilized as described above.

The main component of the second peak was shown by thin layer chromatography to be mostly of lipid nature. To ensure that the main antigenic activity is indeed found in the protein fractions and not in the lipid fractions gametocyte lipids as well as normal chick intestinal lipids were extracted bychloroform-methanol 2:1. Ethanol soluble lipids were analyzed for activity with recovered chick serum, normal chick serum, immune mouse serum and normal mouse serum using both radioimmunoassay (RIA) and ELISA. Water soluble lipids were analyzed with the same sera using the ELISA technique.

Using either technique no specific reactivity to gametocyte lipids was detected using recovered chicken sera or immune mouse sera. Thus it is concluded that gametocyte lipids are not an important component of the immune response to the parasite.

EXAMPLE 7

Monoclonal antibodies to gametocyte antigens

The theory of monoclonal antibody production is based on the clonal hypothesis of Mcfarlane Burnet (32). Ever since Kohler and Milstein routinely achieved hybridomas (33), their protocol is the method of choice for the production of monoclonal antibodies. The Kohler-Milstein method has been used to produce monoclonal antibodies to gametocyte antigens. The monoclonal antibodies obtained will be immobilized on affinity columns and used to obtain large quantities of the required antigens from DOC-extracts (see Example 6).

The first monoclonal antibody was isolated by priming a Balb/C mouse 4 times with an intraperitoneal injection of 150,000 purified gametocytes. A fifth injection of a gametocyte NP-40 extract (see Example 1) was given intrasplenic. The mouse was sacrificed 4 days after the last injection and its spleen cells fused to myeloma cells according to published procedures (34). Monoclonal antibody 2B8-10 ($2^{nd}$ plate, row B, well 8, $10^{th}$ fusion) was tested for activity by the ELISA technique and found to react strongly to gametocyte antigen, to a lesser extent also to control chicken intestine. To exclude the possibility that 2B8–10 might consist of more than one clone, the cells were subcloned and retested. The second monoclonal antibody E9–10 was thus isolated, tested by ELISA and shown to react to gametocyte antigen only. Both supernatant of E9–10 cells, ascites fluid and the IgG-fraction thereof (precipitated by 40% ammonium sulphate) showed one single band in Western blots reacting only with the 56 Kd protein described in Example 6.

The next monoclonal antibody described is 1C3-23. It was derived by injecting a Balb/C mouse twice with fractions of a Sephadex G-200 column. (see Example 6) containing a pool of the first peak and the trough fractions. The third and last injection into this mouse was with a 50% ammonium sulphate cut (see Example 6). 1C3-23 reacted on ELISA plates with gametocyte antigen only and did not show any response to control intestine. On Western blots, 1C3-23, like E9–10, reacts with one single band to the 56 Kd protein.

An additional monoclonal antibody was isolated, which also reacted to the 56 Kd protein band, namely 6B3–27. In contrast to 1C3–23 the third injection into the recipient mouse was with pooled trough fractions only. In neither ELISA test nor in Western blots was any reaction to control intestine detected.

An additional monoclonal antibody 1E11-11, was derived from a Balb/C mouse that had been injected 5 times intraperitoneally with an average of 150,000 purified gametocytes per injection. In both ELISA and Western blots this monoclonal antibody reacted very strongly to gametocyte antigen only. In Western blots one heavy band of 56 Kd was detected. By immunofluorescence studies 1E11-11 reacted specifically with the gametocyte surface only.

A very different approach was taken for a new series of fusions namely, mice were injected with gelpieces from SDS-PAGE. The first such fusion was done with the spleen of a mouse which had received three injections of gelpieces that contained the protein of 82 Kd (see Example 4). The polyclonal serum of this mouse, taken before sacrifice showed a very strong response to the 82 Kd protein band on Western blots as expected.

Three monoclonal antibodies to the 82 Kd protein were obtained from this fusion experiment (1A-1, 1A-2 and 1A-3). These monoclonal antibodies along with the 4 others described above can be used to affinity purify the 56 Kd and 82 Kd antigens from a gametocyte detergent extract.

Hybridomas producing each of the above seven monoclonal antibodies were deposited with the American Type Culture Collection (ATCC), Rockville, Md., U.S.A. 20852 on Aug. 7, 1987 and allotted the following ATCC accession numbers:

|  | ATCC No. |
| --- | --- |
| E9-10 | HB 9556 |
| 1C3-23 | HB 9555 |
| 6B3-27 | HB 9557 |
| 1E11-11 | HB 9558 |
| 1A-1 | HB 9552 |
| 1A-2 | HB 9553 |
| IA-3 | HB 9554 |

These deposits were made pursuant to the provisions of the Budapest Treaty on the International Recognition of the Deposit of Microorganisms for the Purposes of Patent Procedure.

Monoclonal antibody 1E11-11 was found to be IgM type antibody. It was bound to CNBr activated Sepharose 4B (Pharmacia, Upsala, Sweden), and used to affinity purify the 56 Kd antigen from DOC extracted gametocyte proteins. The eluted antigen was tested by Western blotting and shown to be intact and pure.

EXAMPLE 8

Passive immunization of chickens using mouse monoclonal antibodies to *E. maxima* gametocyte antigens 14 day post-infection sera (referred to in this patent as "recovered chicken serum") can be used to passively immunize chickens against *E. maxima* challenge infections (Rose, et al. (5, 7, 8,)). This type of sera was used as the positive control for the mouse monoclonal antibodies, which were tested for their ability to passively immunize chickens against *E. maxima*. These monoclonal antibodies are described in Example 7, and one of them (1E11–11) has already shown its ability to inhibit growth of gametocytes in vitro.

First, the conditions for the challenge infection were established by carrying out a titration curve of 50, 100 and 500 sporulated *E. maxima* oocysts of the Houghton strain to infect 2 week old chickens. Oocyst counts were made on days 6–7, 7–8 and 8–9 post-infection on groups of 20–25 chickens. It was found that the mean output of the 50 oocyst group was lowest, while the standard deviation was not higher than that of the other groups. Therefore, this dosage level was chosen to challenge birds in subsequent experiments.

The first passive immunization experiment was carried out by infecting 2 week old chickens on day 0, then injecting IV either recovered chicken serum or normal chicken serum (0.5–2.0 ml) on days 3–7 p.i. and collecting oocysts in 2% potassium dichromate on days 6–9 p.i. The oocysts were counted and the results are summarized in Table 7. As can be seen, the birds immunized with RCS had a lower mean oocyst count than either the NCS or untreated groups (this result was repeated 3 times). Furthermore, the standard deviation of the RCS group was much lower than the other two groups. Based on the analysis of variation (ANOVA) test, the difference in the means of untreated group and RCS group were statistically significant at the $p<0.05$ level.

The next passive immunization experiment was performed using the monoclonal antibody 1E11-11 (Example 7). A 30% ammonium sulphate cut of 1E11-11 ascites as well as ascites from control myeloma cells (653) were prepared. 2 week old chickens were infected on day 0 and the ammonium sulphate cuts were then injected IV (0.5 ml per injection) on days 4–6 post infection. Oocysts were collected on days 6–9 p.i. and counted on day 9. The results are shown in Table 8. The mean and standard deviation of the group receiving 1E11–11 was much lower than that of the control group and by the ANOVA test was significantly different at the $p<0.05$ level. Furthermore, this inhibition was as good if not better than that seen using RCS, indicating that the 56 Kd protein is the most important antigen in terms of protective immunity.

In the two experiments described above, background variability was found to be a problem in achieving reproducible, statistically significant results. In order to solve this problem, attention was focused on the contribution of maternal antibodies. As shown in Example 4, chicks from commercial suppliers contain different amounts of maternal antibody to gametocyte antigens. Therefore, in order to produce more homogeneous groups of chicks, laying hens from field flocks were placed in clean cages and treated with coccidiostat drugs for 2 to 3 months until their background level of anti-gametocyte antibody was undetectable on Western blots. Offspring from these laying hens were then used to conduct the last three experiments (experiments 2–4, Table 9). As can be seen in Table 9, the results showed once again a 40 to 50% reduction in total oocyst output when 1E11-11 monoclonal antibody was used (both ascites and purified IgM) in comparison with results in chicks either sham immunized with phosphate-buffered saline or immunized with a purified IgM monoclonal antibody, 2B8, produced against an irrelevant T-cell antigen (experiments 2 and 3). Furthermore, because of the much lower variability seen in the groups, these results were now significant at the $P<0.001$ level.

In the last experiment (experiment 4), specific anti-56-Kd protein and anti-S2-Kd protein immune chicken IgG was used. There was a 49% inhibition in oocyst output, similar to the results obtained by using the monoclonal antibody 1E11-11 alone. These results suggest that the protection conferred by antibodies to both the 56 Kd antigen and the 82 Kd antigen is not significantly greater than the protection observed when the anti-56-Kd monoclonal antibody was used alone.

TABLE 7

Individual results with group summaries

| CONTR. GROUP BIRD # | TOTAL OOCYSTS | NCS GOUP BIRD # | TOTAL OOCYSTS | RCS GROUP BIRD # | TOTAL |
|---|---|---|---|---|---|
| 1049 | 2.1E+07 | 1017 | 2.3E+07 | 1021 | 1.6E+07 |
| 1075 | 2.1E+07 | 1067 | 1.5E+07 | 1007 | 1.1E+07 |
| 1095 | 1.9E+07 | 1020 | 1.3E+07 | 1025 | 8.7E+06 |
| 1082 | 1.5E+07 | 1062 | 1.1E+07 | 1036 | 8.6E+06 |
| 1079 | 1.1E+07 | 1074 | 1.0E+07 | 1014 | 7.0E+06 |
| 1064 | 9.5E+06 | 1038 | 9.3E+06 | 1055 | 6.5E+06 |
| 1090 | 9.5E+06 | 1011 | 5.8E+06 | 1055 | 6.5E+06 |
| 1065 | 9.2E+06 | 1046 | 5.1E+06 | 1006 | 6.4E+06 |
| 1068 | 8.3E+06 | 1058 | 4.8E+06 | 1022 | 6.2E+06 |
| 1092 | 6.2E+06 | 1033 | 4.5E+06 | 1050 | 5.0E+06 |
| 1047 | 5.1E+06 | 1087 | 4.4E+06 | 1028 | 4.3E+06 |
| 1040 | 4.9E+06 | 1088 | 4.3E+06 | 1100 | 3.7E+06 |
| 1042 | 4.8E+06 | 1089 | 3.2E+06 | 1069 | 3.2E+06 |
| 1054 | 4.3E+06 | 1027 | 3.0E+06 | 1043 | 2.9E+06 |
| 1037 | 4.0E+06 | 1099 | 2.6E+06 | 1091 | 2.1E+06 |
| 1030 | 3.8E+06 | 1059 | 2.3E+06 | 1086 | 1.3E+06 |
| 1085 | 3.7E+06 | 1051 | 2.3E+06 | 1016 | 1.1E+06 |
| 1072 | 2.8E+06 | 1078 | 2.3E+06 | 1015 | 8.0E+05 |
| 1061 | 2.7E+06 | 1003 | 2.3E+06 | 1093 | 8.0E+05 |
| 1056 | 2.6E+06 | 1035 | 2.0E+06 | 1002 | 7.0E+05 |
| 1001 | 2.1E+06 | 1018 | 1.6E+06 | 1077 | 4.0E+05 |
| 1063 | 2.0E+06 | 1084 | 3.0E+05 | 1045 | 2.0E+05 |
| mean= | 7.9E+06 | mean= | 6.0E+06 | mean= | 4.7E+06 |
| SD= | 6.0E+06 | SD= | 5.3E+06 | SD= | 3.9E+06 |
| n= | 22 | n= | 22 | n= | 22 |

TABLE 8

| 653 BIRD # | OOCYST OUTPUT (Millions) | 1E11-11 BIRD # | OOCYST OUTPUT (Millions) | 653 BIRD # | OOCYST OUTPUT (Millions) | 1E11-11 BIRD # | OOCYST OUTPUT (Millions) |
|---|---|---|---|---|---|---|---|
| 1378 | 14.6 | a1 | 3.4 | 1407 | 10.7 | 1469 | 3.7 |
| 1416 | 20.2 | 1340 | 1 | 1328 | 0.9 | 1401 | 6.1 |
| 1437 | 3.5 | 1476 | 3.3 | 1448 | 7 | 1444 | 5.7 |
| 1500 | 1.9 | 1395 | 2.5 | 1406 | 5.4 | 1327 | 0.4 |
| 1453 | 6 | 1410 | 6.5 | 1415 | 1.4 | 1474 | 1.5 |
| 1310 | 4.8 | 1377 | 6.3 | 1432 | 3.8 | 1430 | 1.3 |
| 1358 | 5.4 | 1424 | 1.5 | c23 | 16.7 | 1326 | 0.9 |
| 1323 | 2.5 | 1408 | 4.7 | c27 | 8.9 | 1319 | 2 |
| 1455 | 2.3 | 1440 | 3.6 | Mean= | 5.95 | Mean= | 3.60 |
| 1481 | 3.5 | 1374 | 10.1 | SD= | 5.00 | SD= | 2.40 |
| b8 | 2.9 | 1480 | 1.1 | n= | 25 | n= | 25 |
| 1330 | 0.9 | b15 | 5.3 | | | | |
| 1338 | 2.4 | 1306 | 1 | | | | |
| 1403 | 3.5 | 1390 | 2.5 | | | | |
| 1429 | 4.1 | 1369 | 5.8 | | | | |
| 1413 | 11.5 | 1450 | 6.7 | | | | |
| 1447 | 3.9 | c1 | 3.2 | | | | |

TABLE 9

Summary of passive immunization results using monoclonal and polyclonal antibodies

| Expt. no. | Control group | Oocyst[a] counts ($\times 10^{-6}$) | Experimental group | Oocyst counts ($\times 10^{-6}$) | Percent reduction | Level of[b] Significance (pc) |
|---|---|---|---|---|---|---|
| 1 | 653 ascites | 5.9 ± 5.0 | 1E11-11 ascites | 3.6 ± 2.4 | 40 | 0.05 |
| 2 | PBS | 15.1 ± 5.2 | 1E11-11 IgM[c] | 8.7 ± 3.4 | 43 | 0.001 |
| 3 | 2B8 IgM | 8.4 ± 3.7 | 1E11-11 IgM | 5.1 ± 2.2 | 39 | 0.001 |
| 4 | PBS | 2.4 ± 1.9 | Immune sera[d] | 1.2 ± 1.0 | 49 | 0.02 |

[a]Mean ± standard deviation with 20–25 chicks per group.
[b]Significance as determined by the student t test.
[c]IgM of monoclonals prepared by ammonium sulphate precipitation as described in Materials and Methods.
[d]Immune sera refers to immune chicken sera prepared against the affinity purified 56 Kd and 82 Kd antigens.

EXAMPLE 9 cDNA cloning of the major E. maxima gametocyte antigens

It is of importance to clone the genes encoding the major protective antigens described in this patent in order to be able to produce them in large quantities by fermentation. The first step in this process is to be able to correlate those antigens seen by Western blotting to those obtained in cell-free translation products. To this end we used F 33 mouse polyclonal antiserum to the 82 Kd protein, 1E11–11, which reacts specifically to the 56 Kd antigen, and affinity purified chicken anti cytochrome C which binds the 43 Kd protein in order to perform immune precipitation of the cell-free translation products. It was found that F 33 reacted with 100 Kd translated protein, 1E11–11 bound the 45 Kd protein and chicken anti cytochrome C recognized the 65 Kd translation product. We next prepared a cDNA library in the lambda vector, lambda zap of Stratagene (La Jolla, Calif.).

The library was screened with the various monoclonal antibodies and polyclonal immune sera described above along with polyclonal antibodies prepared against the 56 Kd and 82 Kd affinity purified *E. maxima* gametocyte antigens.

Two clones recognized by polyclonal antisera F33 (λEM 82/3 and λEM82/4), one clone recognized by monoclonal antibody 1E11-11 (λEM56/1), and two clones recognized by the mouse polyclonal antibodies to the 56 Kd and 82 Kd gametocyte antigens (λEM 56/2 and λEM 56/3) were obtained. In addition, clone λEM 250/14 was isolated from the cDNA library using clone λEM 82/4 as a probe to screen the library. Clones λEM 82/3, λEM 82/4 and λEM 56/1 were deposited on Feb. 12, 1988 with the American Type Culture Collection (ATCC), Rockville, Md., U.S.A. 20852.

Clones pEM250/14, pEM 56/2, and pEM 56/3 (plasmids derived from clones λEM 250/14, λEM 56/2 and λEM 56/3) were deposited with the ATCC on Feb. 12, 1990. These clones were allotted the following ATCC accession numbers:

|           | ATCC No. |
|-----------|----------|
| λ EM 82/3 | 40424    |
| λ EM 82/4 | 40425    |
| λ EM 56/1 | 40423    |
| pEM 250/14| 68229    |
| pEM 56/2  | 68227    |
| pEM 56/3  | 68228    |

These deposits were made pursuant to the provisions of the Budapest Treaty on the International Recognition of the Deposits of Microorganisms for the Purposes of Patent Procedure.

All of the clones described above were characterized using a few or all of the following techniques: hybrid select translation, Southern and Northern blotting and sequence analysis.

Clone λ EM 82/4 was used to perform hybrid select translation as follows: The λ clone was first converted into the plasmid pEM 82/4 using the automatic excision process built into the λ zap vector system (Stratagene, LaJolla, Calif.). The plasmid DNA was bound to nitrocellulose filters and used to hybrid select its corresponding mRNA from total gametocyte RNA. The mRNA was then translated in a rabbit reticulocyte cell free system, and the products were analyzed by SDS polyacrylamide gel electrophoresis and autoradiography. As controls, pBluescript plasmid DNA containing no detectable insert, and RNA from uninfected chicken intestine were used. The results are shown in FIG. 8. As can be seen only the gametocyte mRNA which was selected using the clone pEM 82/4 DNA (lanes 5–7), showed a 250 Kd band which was absent from both controls using pBluescript DNA (lanes 2–4), and uninfected intestine mRNA with clone pEM 82/4 DNA (not shown). It was therefore concluded that the clones λ EM 82/3, λ EM 82/4 and λ EM 250/14 contain sequences encoding a portion of the 250 Kd *E. maxima* gametocyte antigen. Since, restriction endonuclease mapping indicated that λ EM 82/3 and λ EM82/4 were identical clones, only λ EM82/4 and pEM 250/14 were employed for the studies described below.

On Southern blots of *E. maxima* gametocyte DNA of an American strain #68, clone pEM 250/14 hybridized with a single EcoR1 band and a single Pst I band of about 9.4 KB and 5.6 KB in size respectively (FIG. 9). Using the four base cutting restriction endonuclease Alu I, 4 bands were observed of 200–500 base pairs in size. Furthermore, clone λ EM 82/4 was found to hybridize to bands of the same size in *E. maxima* gametocyte DNA of the Houghton strain from England, and also cross-hybridized with oocyst DNA from *E. tenella* and *E. acervulina* (not shown). These results indicate that not only is this gene conserved between strains of *E. maxima* but also between Eimerian species as discussed previously.

On Northern blots, clones pEM 82/4 and pEM 250/14 mainly reacted with a messenger RNA molecule of about 7 KB in size (FIG. 10). They did not react whatsoever with uninfected chicken intestine RNA used as a control (lane 6), and pBluescript plasmid DNA used as a control probe also did not react with gametocyte RNA (not shown). Based on these results it was concluded that the 250 kD *E. maxima* antigen is encoded by an mRNA of about 7 KB in size.

Clone λ EM 56/1 was also used as a probe on Northern blots. No hybridization with gametocyte RNA was detected and upon further restriction enzyme analysis it was found that this clone contained a very short (50–100 bp) insert. We therefore chose to concentrate on the other clones which were isolated using antibodies to the affinity purified 56 Kd and 82 Kd antigens (pEM 56/2 and pEM 56/3) to characterize the gene(s) and mRNA(s) encoding these two proteins.

Clone pEM 56/2 was used as a probe on Southern blots of *E. maxima* DNA and the results are shown in FIG. 9. As can be seen using three restriction endonucleases, EcoRI, PstI and AluI, all three enzymes produced a smear of hybridizing bands of both high and low molecular weights. Using EcoRI there was a 10 KB band which stood out above the background smear.

On Northern blots, clone pEM 56/2 reacted with three *E. maxima* gametocyte mRNA species of about 3.5 KB, 2.2 KB and 0.7 KB in size (FIG. 10). It reacted with mRNAs of the same size in RNA from gametocyte containing infected intestine while it did not react at all with RNA from uninfected intestine (lane 12). Based on the sizes of the mRNAs and in vitro cell-free translation products (see above), we predicted that the 3.5 KB and the 2.2 KB mRNAs probably encode the 82 Kd and 56 Kd gametocyte antigens respectively.

Clone pEM 56/3 was used as a probe on Northern blots and found to react with two gametocyte mRNAs of about 3.5 KB and 2.2 KB in size. These mRNAs were similar in size to two of the mRNAs recognized by clone pEM 56/2. Based on the sequence of clones pEM56/2 and 56/3 (see below) it appears that clone pEM 56/2 encodes the 0.7 KB mRNA while clone pEM 56/3 encodes for either the 2.2 KB or 3.5

KB mRNA. Work is in progress to screen the gametocyte cDNA library with these two clones in order to obtain the full length sequence of these three mRNAs.

Sequence analysis of clones pEM 250/14, pEM 56/2 and pEM 56/3 was carried out and the results are summarized in FIGS. 11–14. As can be seen in FIGS. 11 and 12, clone pEM 250/14 has open reading frames at both the 5' and 3' ends of the insert. In FIG. 11 the first 293 nucleotides of the 5' portion of the insert is shown and it contains a 42 nucleotide tandem repeat. This sequence was compared with all the sequences in the gene bank and no other gene was found having significant homology with this gene. The last 196 nucleotides of the insert are shown in FIG. 12. As can be seen this sequence is non-repetitive and contains a potential glycosylation site Asn-Cys-Ser. Work is now in progress to sequence the rest of the insert and predict the entire open reading frame.

FIG. 13 shows the complete sequence of clone pEM56/2. It contains the entire coding region of the 0.7 KB mRNA seen on the Northern blots (see above) and encodes a 76 amino acid polypeptide which is very rich in alanine (30%) and leucine (18%). This sequence was also searched against the gene bank and the only protein of significant homology to this gene was an antifreeze peptide from the winter flounder. The significance of this homology remains to be determined. Clone pEM 56/2 contains the consensus AATAAA polyadenylation signal (overlined) and based on comparison with the sequence of antifreeze proteins have two potential glycosylation sites Ala-Thr-Ala which in antifreeze proteins are linked to n-acetyl galactosamine (the same sugar which is recognized by Soybean lectin).

FIG. 14 shows the complete sequence of clone pEM56/3. It represents the 3' half of either the 2.0 or 3.5 KB mRNAs and contains the poly A tail. There are two possible open reading frames which are presented in FIGS. 14a and 14b. Work is in progress to clone the full length cDNA and once the sequence is determined the actual reading frame will be predicted.

EXAMPLE 10

Active immunization of chickens against *E. maxima* infection using affinity purified gametocyte antigens and gametocyte antigen produced by cDNA cloning Active immunization experiments were carried out using the major protective antigens described in this patent application. It has already been shown that whole gametocytes can give partial protection against challenge infections in 6 week old chickens (Example 2), and that antisera or monoclonal antibodies to the 56 Kd antigen can give passive immunization in young chicks (Example 8). In the present Example, we attempted to show that by active immunization of one day old chicks the three major gametocyte antigens having molecular weights of 82 Kd, 56 Kd, and 250 Kd have the ability to protect against *E. maxima* infections. These antigens were prepared by affinity chromatography as described in Examples 5 and 7.

The conditions for the experiment were first established by carrying out a titration experiment similar to the one described in Example 8, however, chickens were challenged with the FS 110 strain of *E. maxima* isolated at Merck, Inc., Rahway, N.J., U.S.A. The results of the titration curve showed that the optimal challenge dosage was approximately 100 *E. maxima* sporulated oocysts.

The actual immunization protocol was as follows: Birds used in the test were 2 day old Peterson X Arbor Acre males. Twenty birds per group were immunized with 100 ng of soybean lectin affinity purified antigens (Aff. Pur.) precipitated with alum or 1–2 mg of total gametocyte extract (Extract) precipitated with alum and injected intrasmuscularly on days 2, 9 and 16. On day 17 the birds were challenged with 100 FS 110 sporulated oocysts and feces were collected on days 23, 24 and 25 for measurement of oocyst output (i.e. days 6–8 post-challenge). A control group was sham immunized with Alum alone (Inf. Co.) and an additional group served as non-infected controls (Normals). Sera were collected on days 1 and 22 and tested for their reactivity with gametocyte antigen on Western blots.

The results of oocyst counting are summarized in Table 10. As can be seen there was essentially no difference between the experimental and control groups. However, it is of interest to note that one of the immunized chicks from the affinity purified antigen group showed 0 oocyst output throughout the experiment (it is unusual to find 0 oocyst output in any of these experiments). Another chick in that group was exceptionally low where only 1 oocyst was counted in the fecal samples in the 3 days of counting. Whether or not there is any significance to this is not clear.

By Western blotting, it was found that the 22 day sera from immunized chicks showed little or no reactivity with gametocyte antigens especially in comparison with sera from 6 week old chickens which were immunized with the same affinity purified antigens in Isreal. From these results, it was concluded that the lack of protection found using the affinity purified gametocyte antigens to immunize chicks was due to the inability of such young chicks to mount an effective antibody response.

Finally, sera from preimmune one day old chicks reacted strongly with the *E. maxima* Houghton strain gametocyte antigens. These results indicate that the low response seen at 22 days of age was not due to a genetic inability of this breed of chicken to respond to the antigens, but rather is related to the age of immunization. Furthermore, the presence of antibodies to gametocyte antigens of the Houghton strain of *E. maxima* in newborn chick sera from an American chicken, indicate that these antigens are well conserved between different strains of *E. maxima* as was discussed in Example 5.

EXAMPLE 11

Experiments Demonstrating Maternal Immunity as a Means Immunizing Chickens Against *E. Maxima* and Other Eimeria Species In Example 8, a series of passive immunization experiments were carried out showing that both polyclonal and monoclonal antibodies to Eimeria spp. 56 Kd and 82 Kd antigens injected into chicks can provide protection against challenge infections.

Furthermore, the results described above in Example 13 had indicated that attempts at active immunization of one day old chicks did not induce protective immunity nor was there an appropriate antibody response elicited through this type of vaccination. Therefore, in order to overcome the difficulty inherent in active immunization of young chicks and to provide large amounts of specific antibody to newly hatched chicks via the yolk, maternal immunity was employed as described below.

The following experiments were carried out in order to demonstrate the effectiveness of such an approach:

1. Antigen vaccinations. Affinity purified 56 Kd and 82 Kd gametocyte antigens were used to vaccinate laying hens which had been treated for several months with coccidiostat drugs and maintained coccidia free. These injections of about 50 ng each were administered intramuscularly in complete Freund's adjuvant followed by two boosts of antigen in incomplete Freund's at weekly intervals. As controls, 10 layers were sham immunized with PBS in Freund's as above (negative control), and 7 layers were given a live infection with 50,000 oocysts (positive control). In the first experiment chicks from field hens were used as a control group due to a drop in egg production in the PBS sham immunized group. In addition, the infected group was kept 10 at a separate chicken house in order to avoid contamination of the vaccinated, coccidia free layers. The hens were artificially inseminated, the fertilized eggs were collected and placed in incubators for hatching. Sera from layers and yolks from eggs of each group were tested by Western blotting in order to demonstrate the presence of anti-gametocyte antibodies in the hens and eggs.

Figure 15:
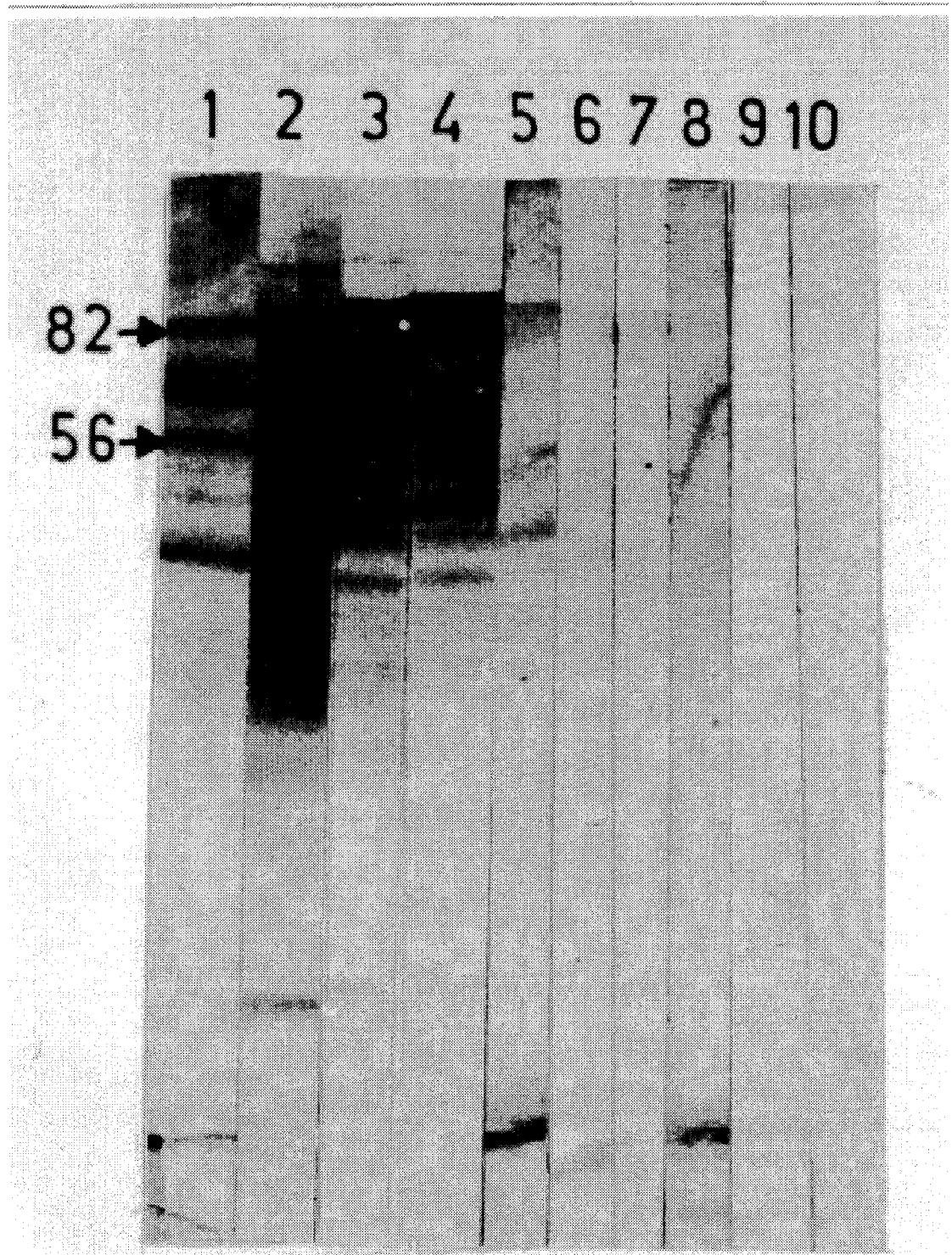
FIG. 15 shows the results of a preparative Western blot containing *E. maxima* gametocyte antigen reacted with yolks from eggs laid by hens immunized with soybean lectin affinity purified antigens (Lanes 2–4) or PBS (Lanes 5–10). Yolks were diluted at either 1:100 (Lanes 2,5,8), 1:500 (Lanes 3,6,9) or 1:1600 (Lanes 4,7,10). Lane 1 was a positive control using recovered chicken serum at 1:100. Numbers at left indicate the major 56 Kd and 82 Kd *E. maxima* gametocyte antigens.

The results of the Western blot showed that the sera and yolks from hens which were immunized with the affinity purified antigens (purified either using the monoclonal antibody 1E11-11 or soybean lectin agarose), had high titers of anti 56 Kd and anti 82 Kd gametocyte antibodies (FIG. 15) whereas those from PBS sham immunized controls showed virtually no response.

2. Protection studies. In the first experiment, chicks from immunized and control hens were challenged at 3 days of age with 100 sporulated *E. maxima* oocyst and feces were collected from days 6–9 post-infection. Oocyst counts were performed and the results are summarized in Table 11. As can be seen, all three immunized groups showed marked reductions in oocyst output. The soybean lectin and monoclonal antibody affinity purified antigen groups combined gave an 83% reduction in oocyst output as compared to the commercially available group of untreated chicks (this difference is statistically significant at the $p<0.001$ level). In addition, in 2 out of 11 of the chicks from hens immunized with the affinity purified antigens, we were unable to detect any oocysts in the feces, whereas none of the 29 chicks in the control group has 0 oocyst output (0 meaning below our level of detection using conventional counting methods).

Finally, the levels of inhibition achieved using our affinity pure gametocyte antigens was equal to or even greater than that seen in chicks of hens immunized by a live infection (reduction of 76.5%, similar to the results obtained by Rose & Long using live infections to protect against *E. tenella* (4)).

Sera were taken from the chicks at the end of the experiment when they were 12 days of age, and were analyzed by Western blotting. Most of the sera from chicks of immunized hens showed a strong reactivity with the 56 Kd and 82 Kd antigens. Furthermore, there was a good correlation between reactivity on the Western with oocyst output from individual chicks.

The next experiment was carried out four months later using the same layers (during that period they went through a molt and stopped egg production) without giving them any additional boosts with antigen. The layers were artificially inseminated, the fertilized eggs were set in incubators and the chicks were challenged as described above. As can be seen in Table 12, even after four months in cages and maintained coccidia free, the chicks from hens immunized with the affinity pure antigens, still showed a statistically significant level of protection. Although only a 23–27% reduction in oocyst output was observed, in absolute numbers there was an average reduction in oocyst output of $2-2.5\times10^6$ oocysts. Since the average number of oocysts shed in the control group was much higher than that seen in the first experiment, it is possible that with smaller challenge dosage levels more significant levels of inhibition would have been obtained. Nonetheless, this experiment demonstrates that the immunity induced by gametocyte antigens is long-lasting even when birds are drug treated and kept in cages.

The third experiment was performed using the same laying hens, however, the birds were given one additional boost prior to fertilization and collection of eggs. As can be seen in Table 12, a more significant level of inhibition (45–60%) was observed with a drop in average oocyst output of $3-4\times10^6$ as compared to the controls.

Sera was taken from 12 of the chicks from maternal experiment #3 when the chicks were 12 days of age. They were analyzed by Western blotting and it was found that chicks from layers immunized with either soybean lectin or 1E11-11 affinity pure antigens showed strong reactivity against the 56 Kd and 82 Kd antigens whereas chicks from the PBS sham immunized group showed virtually no reactivity. Furthermore, in comparing the intensity of reactivity on the Western blot with the oocyst output of 14 individual chicks (9 from immunized hens and 5 from PBS controls), a good correlation between antibody response and protective immunity was found. The results showed that 7 out of 9 of the chicks from immunized hens strongly reacted with the 56 Kd and 82 Kd gametocyte antigens on Western blots, and had an average oocyst output of $1.87\times10^6$, 70% below that of the average PBS control. The two chicks from immunized hens which showed low reactivity with gametocyte antigens on Western blots both had relatively high oocyst outputs (3.79 and $4.92\times10^6$). The 5 chicks from control PBS hens which were analyzed, showed no reactivity with gametocyte antigens and had very high oocyst outputs with an average of $7.26\times10^6$.

Based on these results the following conclusions were made:

a) Antibodies to the 56 KD and 82 KD gametocyte glycoproteins are highly protective against transmission of *E. maxima* infections in young chicks.

b) Chicks from laying hens raised under field conditions are susceptible to infection with *E. maxima* at 3 days of age in spite of the presence of maternal antibody against gametocyte (and other stage) antigens.

c) Using only 2 affinity-purified antigens, levels of protection as good as if not better than those provided from live infections were achieved.

d) There is a good correlation between protection and anti-gametocyte serum titers.

e) It was previously demonstrated that young chicks from commercial suppliers contain maternally-derived anti-gametocyte antibodies. However, the antibody titer becomes undetectable by 10 days of age. In contrast, using the antigens of the subject invention to immunize laying hens, it was found that the chicks maintained a high antigametocyte titer for at least 12 days. In addition, based on the literature this titer can most likely last for at least 3–4 weeks. Thus, by immunizing laying hens with gametocyte antigens, it should be possible to:
 1) Greatly lower the number of oocysts present in the litter of broiler chicks throughout the course of their growth.

2) Complement immunity to the earlier stages of Eimerian development. The development of parasites escaping immunity to asexual stages would be checked at the gametocyte stage. Furthermore, the "transmission block" provided by gametocyte immunity allows for exposure to asexual stage antigens without the spread of oocysts in the litter.

f) Recently, we have immunized young chicks with gametocyte antigens and have shown that a titer may be achieved at 4 weeks of age. It is therefore believed that with the use of a variety of adjuvants and immunomodulators, a response may be achieved even earlier. Thus, a combination of immunizing laying hens to protect chicks for the first 3–4 weeks of age together with administering antigens to chicks (sporozoite, merozoite and/or gametocyte) upon hatching may be most effective in providing immunity under field conditions.

EXAMPLE 12

Use of Cloned Antigens to Immunize Chicks Via Maternal Immunity

Several cDNA clones expressing the 10 Kd, 56 Kd, 82 Kd and 250 Kd antigens have been isolated (Example 9). Fusion proteins will be produced from these clones and tested by maternal immunization as above. Southern blots using one of the *E. maxima* gametocyte cDNA probes have shown that cross-hybridization exists between *E. maxima* and other Eimerian species at the DNA level (Example 9). These probes may be used to isolate the cross-hybridizing genes and analyze their degree of homology. Should good homology exist, cross species immunization experiments may be carried out with the cloned *E. maxima* antigens alone or perhaps in combination with the homologous gene products.

TABLE 10

Summary of Oocyst Counts

| TREATMENT | DAY 7 | DAY 8 | DAY 9 | TOTAL | CHECK (X + σ) |
|---|---|---|---|---|---|
| EXTRACT[a] | 1.38E+06 | 1.07E+06 | 4.17E+04 | 2.49E+06 | 2.49E+06 |
|  | 1.36E+06 | 1.39E+06 | 7.73E+04 |  | 2.59E+06 |
| AFF. PUR.[b] | 1.59E+06 | 1.22E+06 | 1.39E+05 | 2.95E+06 | 2.95E+06 |
|  | 1.75E+06 | 1.15E+06 | 2.34E+05 |  | 2.61E+06 |
| INF. CO.[c] | 1.85E+06 | 7.34E+05 | 8.77E+04 | 2.67E+06 | 2.67E+06 |
|  | 1.68E+06 | 9.07E+05 | 1.49E+05 |  | 2.01E+06 |
| NORMALS[d] | 0.00E+00 | 0.00E+00 | 0.00E+00 | 0.00E+00 | 0.00E+00 |

[a]EXTRACT — Crude gametocyte extract
[b]AFF. PUR. — Soybean lectin affinity purified 56 kD and 82 kD antigens
[c]INF. CO. — Infected control: birds which were sham immunized with alum and infected
[d]NORMALS — Birds from the same batch of chicks which were infected negative controls

TABLE 11

Summary of Results of the Maternal Immunization Experiment

| Control Groyp | | Live infected | | Anti SBL | | Anti 1E11-11 | |
|---|---|---|---|---|---|---|---|
| Counts | × $10^6$ | Counts | × $10^6$ | Counts | × $10^6$ | Counts | $10^6$ |
| 135 | 4.50 | 36 | 1.20 | 13 | 0.43 | 19 | 0.63 |
| 97 | 3.23 | 23 | 0.77 | 7 | 0.23 | 16 | 0.53 |
| 78 | 2.60 | 12 | 0.40 | 5 | 0.17 | 10 | 0.33 |
| 72 | 2.40 | 12 | 0.40 | 2 | 0.067 | 9 | 0.30 |
| 67 | 2.23 | 11 | 0.37 | 0 | 0.00 | 3 | 0.10 |
| 64 | 2.13 | 6 | 0.20 | x = 5.4 | 0.18 | 0 | 0.00 |
| 58 | 1.93 | 6 | 0.20 | s = 5.0 | 0.17 | x = 9.5 | 0.32 |
| 55 | 1.83 | 5 | 0.17 | % reduction = 88 | | s = 7.3 | 0.24 |
| 55 | 1.83 | 3 | 0.10 | | | % reduction = 78.4 | |
| 54 | 1.80 | 2 | 0.07 | | | | |
| 50 | 1.67 | 0 | 0.00 | Combined Anti SBL, Anti 1E11 | | | |
| 49 | 1.63 | x = 10.5 | 0.35 | x = 0.25 × $10^6$ | | | |
| 49 | 1.63 | s = 10.6 | 0.35 | s = 0.21 × $10^6$ | | | |
| 46 | 1.53 | % reduction = 76.5 | | % reduction = 83.2 | | | |
| 40 | 1.33 | n = 11 | | n = 11 | | | |
| 38 | 1.27 | | | | | | |
| 36 | 1.20 | | | | | | |
| 33 | 1.10 | | | | | | |
| 31 | 1.03 | | | | | | |
| 28 | 0.93 | | | | | | |
| 27 | 0.90 | | | | | | |
| 26 | 0.87 | | | | | | |
| 26 | 0.87 | | | | | | |
| 25 | 0.83 | | | | | | |
| 18 | 0.60 | | | | | | |
| 13 | 0.43 | | | | | | |
| 13 | 0.43 | | | | | | |
| 12 | 0.40 | | | | | | |
| 5 | 0.17 | | | | | | |

TABLE 11-continued

| Summary of Results of the Maternal Immunization Experiment | | | | | | | |
|---|---|---|---|---|---|---|---|
| Control Groyp | | Live infected | | Anti SBL | | Anti 1E11-11 | |
| Counts | $\times 10^6$ | Counts | $\times 10^6$ | Counts | $\times 10^6$ | Counts | $10^6$ |
| x = 44.8 | 1.49 | | | | | | |
| s = 27.8 | 0.93 | | | | | | |
| n = 29 | | | | | | | |

TABLE 12

SUMMARY OF RESULTS OF THE THREE MATERNAL IMMUNIZATION EXPERIMENTS

| | Group | | | | | | | % Reduction | | Significance (P) | |
|---|---|---|---|---|---|---|---|---|---|---|---|
| | PBS | | SBL | | 1E11-11 | | | | | | |
| Exp. # | n | x | s | n | x | s | n | x | s | SBL | 1E11-11 | SBL | 1E11-11 |
| 1 | 29[a] | 1.5 | 0.9 | 11 | 0.2 | 0.2 | (1E11-11 + SBL)[b] | | | 83.2 | 83.2 | 0.001 | 0.001 |
| 2 | 27 | 9.3 | 4.4 | 13 | 6.8 | 3.7 | 16 | 7.2 | 3.1 | 26.9 | 23.0 | 0.02 | 0.05 |
| 3 | 17 | 5.9 | 3.0 | 17 | 3.3 | 1.2 | 20 | 2.6 | 1.3 | 43.7 | 55.4 | 0.001 | 0.001 |

[a]In the first experiment chicks hatched under field conditions were used due to a drop off in egg production by the PBS sham immunized group.
[b]The results listed in the SBL group column represent the combined results of the SBL and the 1E11-11 immunized hens.

REFERENCES

1. Tamas, T., Schleim, K. D. and Olson, G. (1985). Chicken battery study on host immunity and the coccidial life cycle. Poultry Science 64 (Supplement 1), 187.

2. Speer, C. A., Wong, R. B., Blixt, J. A. and Schenkel, R. H. (1985). Capping of immune complexes by sporozoites of *Eimeria tenella*. J. Parasit. 7: 33–42.

3. Long, P. L., Rose, M. E. and Pierce, A. E. (1963). Effects of fowl sera on some stages in the life cycle of *Eimeria tenella*. Exp. Parasit. 14: 210–217.

4. Rose, M. E. and Long, P. L. (1971). Immunity to coccidiosis: protective effects of transferred serum and cells investigated in chick embryos infected with *Eimeria tenella*. Parasitology 63: 299–313.

5. Rose, M. E. (1971) Immunity to coccidiosis: protective effect of transferred serum in *Eimeria maxima* infections. Parasitology 62: 11–25.

6. Long, P. L. and Rose, M. E. (1972). Immunity to coccidiosis: effect of serum antibodies on cell invasion by sporozoite of *Eimeria in vitro*. Parasitology 65: 437–445.

7. Rose, M. E. (1974) Protective antibodies in infections with *Eimeria maxima*: the reduction of pathogenic effects in vivo and a comparison between oral and subcutaneous administration of antiserum. Parasitology 68: 285–292.

8. Rose, M. E. (1974). Immunity to *Eimeria maxima*: Reactions to antisera in vitro and protection in vivo. J. of Parasit. 60: 528–530.

9. Danforth, H. D. and Augustine, P. C. (1983). Specificity and cross-reactivity of immune serum and hybridoma antibodies to various species of avian coccidia. Poultry Sci. 62: 2145–2151.

10. Augustine, P. C. and Danforth, H. D. (1986). Effects of hybridoma antibodies on invasion of cultured cells by sporozoites of *Eimeria*. Avian diseases 29: 1212–1223.

11. Freeman, R. R., Trejdosiewicz, A. J. and Cross, G. A. M. (1980). Protective monoclonal antibodies recognizing stage-specific merozoite antigens of a rodent malaria parasite. Nature 284: 366–368.

12. Perrin, L. H., Ramirez, E., Lambert, P. H. and Miescher, P. A. (1981). Inhibition of *P. falciparum* growth in human erythrocytes by monoclonal antibodies. Nature 289: 301–303.

13. Kouwenhoven, B. and Kuil, H. (1976). Demonstration of circulating antibodies to *Eimeria tenella* by the indirect immunofluorescent antibody test using sporozoites and second-stage schizonts as antigen. Vet. Parasit. 2: 283–292.

14. Rose, M. E. and Hesketh, P. ( 1976). Immunity to coccidiosis: stages of the life-cycle of *Eimeria maxima* which induce, and are affected by, the response of the host. Parasit. 73: 25–37.

15. Carter, R., Gwadz, R. W. and McAuliffe, F. M. (1979). *Plasmodium gallinaceum:* Transmission-blocking immunity in chickens I. Comparative immunogenicity of gametocyte— and gamete—containing preparations. Exp. Parasit. 47: 185–193.

16. Harte, P. G., Rogers, N. C. and Targett, G. A. T. (1985). Monoclonal anti-gamete antibodies prevent transmission of murine malaria. Parasit. immunol. 7: 607–615.

17. Doran, D. J. and Augustine, P. C. (1973). Comparative development of *Eimeria tenella* from sporozoites to oocytes in primary kidney cell cultures from gallinaceous birds. J. Protozool. 20: 658–661.

18. Shirley, M. W., McDonald, V. and Bailingall, S. (1981). *Eimeria* spp. from the chicken: from merozoites to oocytes in embryonated eggs. Parasitology 83: 259–267.

19. Stotish, R. L. and Wang, C. C. (1975). Preparation and purification of merozoites of *Eimeria tenella*. J. Parasit. 61: 700–703.

20. Wallach, M. (1982). Efficient extraction and translation of *Plasmodium falciparum* messenger RNA. Mol. Biochem. Parasitol. 6: 335–342.

21. Chirgwin, J. M., Presbybyla, A. E., MacDonald, R. J. and Rutter, W. J. (1979). Isolation of biologically active ribonucleic acid from sources enriched in ribonuclease. Biochemistry 18: 5294–5299.

22. Krystosek, A., Cawthon, M. and Kabat, D. (1975). Improved methods for purification and assay of eucaryotic messenger ribonucleic acids and ribosomes. J. Biol. Chem. 250: 6077–6084.

23. Pelham, H. R. B. and Jackson, R. J. (1976). An efficient mRNA-dependent translation system from reticulocyte lysates. Eur. J. Biochem. 67:247–256.

24. Wagenbach, G. E. (1969). Purification of *Eimeria tenella* sporozoites with glass bead columns. J. Parasitol. 55: 833–838.

25. Towbin, H. and Gordon, J. (1984). Immunoblotting and dot immunoblotting—Current status and outlook. J. Immunol. Methods 72: 313–340.

26. Horton-Smith, C., Long, P. L., Pierce, A. E. and Rose, M. E. (1983) In: *Immunity to coccidia in domestic animals*, pp. 273–293 (Ed. P. C. C. Garnham and A. E. Pierce) Oxford: Blackwell Scientific Publications.

27. Browning, T. H. and Trier, J. S. (1969). Organ culture of mucosal biopsies of human small intestine. J. Clin. Invest. 48: 1423–1432.

28. Neutra, M. R. (1980). In: *In vitro epithelia and birth defects* Vol. XVI -2, pp. 261–273. (Ed. B. Shannon Danes) Alan R. Liss Inc., New York, N.Y.

29. Nijhout, M. M., and Carter, R. (1978). Gamete development in malaria parasites: bicarbonate-dependent stimulation by pH in vitro. Parasitology 76: 39–53.

30. Danforth, H. (1983). Use of monoclonal antibodies directed against *Eimeria tenella* sporozoites to determine stage specificity and in vitro effect on parasite penetration and development. Am. J. Vet. Res. 44: 1722–1727.

31. Bradford. M. (1976). Anal Biochem. 72: 248

32. Burner F. M. (1959) The clonal selection theory of acquired immunity, Cambridge University Press.

33. Kohler, G. and Milstein C. (1975). Nature 256: 495.

34. Kohler, G. and Milstein C. (1976) Eur. J. Immunol. 6:511.

What is claimed is:

1. A method of reducing the output of Eimeria oocysts in faces from a newborn chick which comprises administering to a laying hen prior to the hen laying a fertilized egg an amount of a purified or recombinant antigenic protein present in gametocytes of an Eimeria spp. effective to induce in the hen an immune response and transmit maternal antibody to the offspring chick so that the output of oocysts from the chick is reduced, wherein the antigenic protein is selected from the group consisting of proteins derived from Eimeria gametocytes and having molecular weights of 250±20kd, 82±10kd, and 56±5kd, as determined under reducing conditions.

2. A method of claim 1, wherein the Eimeria spp. is *Eimeria maxima.*

3. A method of claim 1, wherein the antigenic protein comprises a protein having a molecular weight of about 56 Kd, as determined under reducing conditions.

4. A method of claim 1, wherein the antigenic protein comprises a protein having a molecular weight of about 82 Kd, as determined under reducing conditions.

5. A method of claim 1, wherein the antigenic protein comprises a protein having a molecular weight of about 250 Kd, as determined under reducing conditions.

6. A method of claim 1, wherein the antigenic protein comprises a recombinant protein encoded by pEM 56/2 (ATCC No. 68227).

7. A method of claim 1, wherein the antigenic protein comprises a recombinant protein encoded by pEM 56/3 (ATCC No. 68228).

8. A method of claim 1, wherein the antigenic protein comprises a recombinant protein encoded by pEM 250/14 (ATCC No. 68229).

9. A method of claim 1, wherein the antigenic protein comprises a recombinant protein encoded by λEM 82/4 (ATCC No. 40425).

10. A method of claim 1, wherein the effective amount of antigenic protein is an amount from about 5 ng to about 5000 ng.

11. A method of claim 6, wherein the effective amount of antigenic protein is an amount from about 50 ng to about 100 ng.

12. A method of claim 1, wherein the administration comprises intravenous, intramuscular or intraperitoneal injection.

* * * * *

UNITED STATES PATENT AND TRADEMARK OFFICE
CERTIFICATE OF CORRECTION

PATENT NO. : 5,496,550
DATED : March 5, 1996
INVENTOR(S) : Michael Wallach, et al.

Page 1 of 3

It is certified that error appears in the above-indentified patent and that said Letters Patent is hereby corrected as shown below:

Column 8, line 27, "maybe" should read --may be--.

Column 9, line 32, "10x20-10$^6$" should read --10-20x10$^6$--.

Column 16, line 39, "give, no" should read --give no--.

Column 16, line 56, "bythe" should read --by the--.

Column 21, line 67, "bychloroform" should read --by chloroform--.

Column 33, table 11, "Groyp" should read --Group--.

Column 36, table 11, "Groyp" should read --Group--.

Column 38, line 2, "faces" should read --feces--.

Column 3, line 7, "findings, that" should read --findings that--.

Column 3, line 64, "peptedes" should read --peptides--.

UNITED STATES PATENT AND TRADEMARK OFFICE
CERTIFICATE OF CORRECTION

PATENT NO. : 5,496,550
DATED : March 5, 1996
INVENTOR(S) : Michael Wallach, et al.

It is certified that error appears in the above-indentified patent and that said Letters Patent is hereby corrected as shown below:

Column 3, line 36, "experiment laying" should read --experiment, laying--.

Column 7, line 12, "p bluescript" should read --pBluescript--.

Column 7, line 32, "Alu I" should read --AluI--.

Column 14, line 26, "contaminants," should read --contaminants;--.

Column 16, line 27, "is and Ig" should read --is an Ig--.

Column 17, line 27, "precipitated at" should read --precipitated a--.

Column 17, line 28, "95 Kd and 65 Kd" should read --95 Kd, 65 Kd--.

Column 18, line 45, "gemetocyte" should read --gametocyte--.

UNITED STATES PATENT AND TRADEMARK OFFICE
CERTIFICATE OF CORRECTION

PATENT NO. : 5,496,550
DATED : March 5, 1996
INVENTOR(S) : Michael Wallach, et al.

It is certified that error appears in the above-indentified patent and that said Letters Patent is hereby corrected as shown below:

Column 21, line 65, "fractions gametocyte" should read --fractions, gametocyte--.

Column 22, line 58, "IC3-23 the" should read --IC3-23, the--.

Signed and Sealed this

Twenty-eighth Day of October, 1997

Attest:

BRUCE LEHMAN

*Attesting Officer*  Commissioner of Patents and Trademarks